United States Patent
Pandev et al.

(10) Patent No.: US 10,255,385 B2
(45) Date of Patent: Apr. 9, 2019

(54) MODEL OPTIMIZATION APPROACH BASED ON SPECTRAL SENSITIVITY

(71) Applicants: Stilian Ivanov Pandev, Santa Clara, CA (US); Thaddeus Gerard Dziura, San Jose, CA (US); Meng-Fu Shih, San Jose, CA (US); Lie-Quan Lee, Fremont, CA (US)

(72) Inventors: Stilian Ivanov Pandev, Santa Clara, CA (US); Thaddeus Gerard Dziura, San Jose, CA (US); Meng-Fu Shih, San Jose, CA (US); Lie-Quan Lee, Fremont, CA (US)

(73) Assignee: KLA-TENCOR CORPORATION, Milpitas, CA (US)

( * ) Notice: Subject to any disclaimer, the term of this patent is extended or adjusted under 35 U.S.C. 154(b) by 1295 days.

(21) Appl. No.: 13/781,474

(22) Filed: Feb. 28, 2013

(65) Prior Publication Data

US 2013/0262044 A1 Oct. 3, 2013

Related U.S. Application Data

(60) Provisional application No. 61/616,971, filed on Mar. 28, 2012.

(51) Int. Cl.
*G06F 17/50* (2006.01)
*G03F 7/20* (2006.01)
(Continued)

(52) U.S. Cl.
CPC .......... *G06F 17/5009* (2013.01); *G03F 7/705* (2013.01); *G03F 7/70625* (2013.01);
(Continued)

(58) Field of Classification Search
None
See application file for complete search history.

(56) References Cited

U.S. PATENT DOCUMENTS 6,278,519 B1 8/2001 Rosencwaig et al.
6,734,967 B1 5/2004 Piwonka-Corle et al.
(Continued)

FOREIGN PATENT DOCUMENTS

WO  WO 2006/091361  8/2006

OTHER PUBLICATIONS

V. F. Paz, P. K. Frenner, W. Osten, A. Ovsianikov, K. Obata, and B. Chichkov, "Depth sensitive Fourier-Scatterometry for he characterization sub-100 nm periodic structures" 9 pgs, 2011.*
(Continued)

*Primary Examiner* — Kibrom K Gebresilassie
(74) *Attorney, Agent, or Firm* — Womble Bond Dickinson (US) LLP

(57) ABSTRACT

Model optimization approaches based on spectral sensitivity is described. For example, a method includes determining a first model of a structure. The first model is based on a first set of parameters. A set of spectral sensitivity variations data is determined for the structure. Spectral sensitivity is determined by derivatives of the spectra with respect to the first set of parameters. The first model of the structure is modified to provide a second model of the structure based on the set of spectral sensitivity variations data. The second model of the structure is based on a second set of parameters different from the first set of parameters. A simulated spectrum derived from the second model of the structure is then provided.

31 Claims, 19 Drawing Sheets

(51) Int. Cl.
*G06T 7/00* (2017.01)
*G01N 21/47* (2006.01)

(52) U.S. Cl.
CPC ...... *G06F 17/5077* (2013.01); *G01B 2210/56* (2013.01); *G01N 21/4788* (2013.01); *G03F 7/70616* (2013.01); *G06T 7/0006* (2013.01); *G06T 2207/30148* (2013.01)

(56) References Cited

U.S. PATENT DOCUMENTS

| | | | |
|---|---|---|---|
| 7,031,848 B2 | 4/2006 | Opsal et al. | |
| 7,236,195 B2* | 6/2007 | Quan | H04N 1/48 348/207.99 |
| 7,428,060 B2 | 9/2008 | Jin et al. | |
| 7,460,237 B1 | 12/2008 | Cramer | |
| 7,478,019 B2 | 1/2009 | Zangooie et al. | |
| 7,532,331 B2* | 5/2009 | Kiers | G03F 7/70625 250/559.22 |
| 7,715,019 B2* | 5/2010 | Kiers | G03F 7/70625 356/303 |
| 7,761,178 B2 | 7/2010 | Tian et al. | |
| 7,831,528 B2 | 11/2010 | Doddi et al. | |
| 2002/0038196 A1* | 3/2002 | Johnson | G01N 21/4788 702/179 |
| 2002/0158193 A1* | 10/2002 | Sezginer | G03F 7/70633 250/237 G |
| 2003/0028358 A1* | 2/2003 | Niu | G01B 11/24 703/2 |
| 2004/0017575 A1* | 1/2004 | Balasubramanian | G01N 21/4788 356/625 |
| 2004/0039473 A1 | 2/2004 | Bao et al. | |
| 2004/0070772 A1* | 4/2004 | Shchegrov | G01N 21/211 356/625 |
| 2004/0090629 A1* | 5/2004 | Drege | G01B 11/24 356/445 |
| 2006/0122724 A1* | 6/2006 | Croke | G06Q 10/087 700/121 |
| 2006/0290947 A1 | 12/2006 | Li et al. | |
| 2007/0237512 A1* | 10/2007 | Kusaka | G03B 13/36 396/111 |
| 2007/0239369 A1* | 10/2007 | Funk | G01B 11/24 702/34 |
| 2007/0239383 A1* | 10/2007 | Funk | G01N 21/4788 702/107 |
| 2008/0068616 A1* | 3/2008 | Kiers | G03F 7/70625 356/601 |
| 2008/0077352 A1* | 3/2008 | Willis | G03F 7/70625 702/155 |
| 2008/0077362 A1* | 3/2008 | Willis | G03F 7/70516 702/189 |
| 2009/0083013 A1 | 3/2009 | Li et al. | |
| 2009/0237676 A1* | 9/2009 | Kiers | G03F 7/70625 356/601 |
| 2010/0225913 A1 | 9/2010 | Trainer | |
| 2010/0245807 A1 | 9/2010 | Li et al. | |
| 2011/0288822 A1 | 11/2011 | Veldman et al. | |
| 2011/0307438 A1 | 12/2011 | Fernandez Martinez | |
| 2012/0022836 A1 | 1/2012 | Ferns et al. | |
| 2012/0086940 A1 | 4/2012 | Shih et al. | |
| 2012/0123581 A1* | 5/2012 | Smilde | G03F 7/70483 700/105 |
| 2012/0123748 A1 | 5/2012 | Aben et al. | |
| 2012/0323356 A1* | 12/2012 | Dziura | G01N 21/47 700/121 |
| 2013/0110477 A1* | 5/2013 | Pandev | G03F 7/705 703/2 |
| 2013/0262044 A1 | 10/2013 | Pandev et al. | |
| 2013/0282343 A1* | 10/2013 | Brill | G01B 11/24 703/2 |
| 2013/0304408 A1* | 11/2013 | Pandev | H01L 22/20 702/83 |
| 2014/0358488 A1* | 12/2014 | Lee | G03F 7/70483 702/190 |
| 2015/0058813 A1* | 2/2015 | Kim | G03F 7/70616 716/52 |
| 2017/0090301 A1* | 3/2017 | Verma | G03F 7/70625 |

OTHER PUBLICATIONS

David Gay, "Computing Optimal Locally Constrained Steps," SIAM J, Sci. Stat. Comput., 2:186-197, 1981.
Gavin, H., "The Levenberg-Marquardt method for nonlinear least squares curve-fitting problems," Duke University, Oct. 9, 2013, 17 pages.
International Search Report and Written Opinion of the International Searching Authority dated Sep. 26, 2014, in International Patent Application No. PCT/US2014/040639, 10 pages.
Stefan Finsterle, Michael Kowalsky, "A truncated Levenberg-Marquardt algorithm for the calibration of highly parameterized nonlinear models", Computers & Geosciences, 37:731-738, 2011.
International Search Report and Written Opinion from PCT/US2013/030907 dated Jun. 24, 2013, 15 pgs.
Office Action dated Aug. 31, 2015, in U.S. Appl. No. 14/293,221, 11 pages.

* cited by examiner

MODEL OPTIMIZATION APPROACH BASED ON SPECTRAL SENSITIVITY

CROSS-REFERENCE TO RELATED APPLICATIONS

This application claims the benefit of U.S. Provisional Application No. 61/616,971, filed Mar. 28, 2012, the entire contents of which are hereby incorporated by reference herein.

TECHNICAL FIELD

Embodiments of the present invention are in the field of metrology, and, more particularly, relate to model optimization approaches based on spectral sensitivity.

BACKGROUND

For the past several years, a rigorous couple wave approach (RCWA) and similar algorithms have been widely used for the study and design of diffraction structures. In the RCWA approach, the profiles of periodic structures are approximated by a given number of sufficiently thin planar grating slabs. Specifically, RCWA involves three main operations, namely, the Fourier expansion of the field inside the grating, calculation of the eigenvalues and eigenvectors of a constant coefficient matrix that characterizes the diffracted signal, and solution of a linear system deduced from the boundary matching conditions. RCWA divides the problem into three distinct spatial regions: (1) the ambient region supporting the incident plane wave field and a summation over all reflected diffracted orders, (2) the grating structure and underlying non-patterned layers in which the wave field is treated as a superposition of modes associated with each diffracted order, and (3) the substrate containing the transmitted wave field.

The accuracy of the RCWA solution depends, in part, on the number of terms retained in the space-harmonic expansion of the wave fields, with conservation of energy being satisfied in general. The number of terms retained is a function of the number of diffraction orders considered during the calculations. Efficient generation of a simulated diffraction signal for a given hypothetical profile involves selection of the optimal set of diffraction orders at each wavelength for both transverse-magnetic (TM) and/or transverse-electric (TE) components of the diffraction signal. Mathematically, the more diffraction orders selected, the more accurate the simulations. However, the higher the number of diffraction orders, the more computation is required for calculating the simulated diffraction signal. Moreover, the computation time is a nonlinear function of the number of orders used.

The input to the RCWA calculation is a profile or model of the periodic structure. In some cases cross-sectional electron micrographs are available (from, for example, a scanning electron microscope or a transmission electron microscope). When available, such images can be used to guide the construction of the model. However a wafer cannot be cross sectioned until all desired processing operations have been completed, which may take many days or weeks, depending on the number of subsequent processing operations. Even after all the desired processing operations are complete, the process to generate cross sectional images can take many hours to a few days because of the many operations involved in sample preparation and in finding the right location to image. Furthermore the cross section process is expensive because of the time, skilled labor and sophisticated equipment needed, and it destroys the wafer.

Thus, there is a need for a method for efficiently generating an accurate model of a periodic structure given limited information about that structure, a method for optimizing the parameterization of that structure and a method of optimizing the measurement of that structure.

SUMMARY

Embodiments of the present invention include model optimization approaches based on spectral sensitivity.

In an embodiment, a method of optimizing parametric models for structural analysis using metrology of repeating structures on a semiconductor substrate or wafer includes determining a first model of a structure. The first model is based on a first set of parameters. A set of spectral sensitivity variations data is determined for the structure. Spectral sensitivity is determined by derivatives of the spectra with respect to the first set of parameters. The first model of the structure is modified to provide a second model of the structure based on the set of spectral sensitivity variations data. The second model of the structure is based on a second set of parameters different from the first set of parameters. A simulated spectrum derived from the second model of the structure is then provided.

In another embodiment, a machine-accessible storage medium has instructions stored thereon which cause a data processing system to perform a method of optimizing parametric models for structural analysis using metrology of repeating structures on a semiconductor substrate or wafer. The method includes determining a first model of a structure. The first model is based on a first set of parameters. A set of spectral sensitivity variations data is determined for the structure. Spectral sensitivity is determined by derivatives of the spectra with respect to the first set of parameters. The first model of the structure is modified to provide a second model of the structure based on the set of spectral sensitivity variations data. The second model of the structure is based on a second set of parameters different from the first set of parameters. A simulated spectrum derived from the second model of the structure is then provided.

In another embodiment, a system to generate a simulated diffraction signal to determine process parameters of a wafer application to fabricate a structure on a wafer using optical metrology includes a fabrication cluster configured to perform a wafer application to fabricate a structure on a wafer. One or more process parameters characterize behavior of structure shape or layer thickness when the structure undergoes processing operations in the wafer application performed using the fabrication cluster. Also included is an optical metrology system configured to determine the one or more process parameters of the wafer application. The optical metrology system includes a beam source and detector configured to measure a diffraction signal of the structure. The optical metrology system also includes a processor configured to determine a first model of a structure, the first model based on a first set of parameters, configured to determine a set of spectral sensitivity variations data for the structure wherein spectral sensitivity is determined by derivatives of the spectra with respect to the first set of parameters, configured to modify the first model of the structure to provide a second model of the structure based on the set of spectral sensitivity variations data, the second model of the structure based on a second set of parameters different from the first set of parameters, and configured to provide a simulated spectrum derived from the second model of the structure.

DETAILED DESCRIPTION

Model optimization approaches based on spectral sensitivity are described herein. In the following description, numerous specific details are set forth, such as specific approaches to performing a sensitivity analysis, in order to provide a thorough understanding of embodiments of the present invention. It will be apparent to one skilled in the art that embodiments of the present invention may be practiced without these specific details. In other instances, well-known processing operations, such as fabricating stacks of patterned material layers, are not described in detail in order to not unnecessarily obscure embodiments of the present invention. Furthermore, it is to be understood that the various embodiments shown in the figures are illustrative representations and are not necessarily drawn to scale.

One or more embodiments described herein are directed to model optimization methods based on spectral sensitivity. Uses for such methods may include, e.g., applications for metrology, such as optical metrology.

One ore more embodiments of the present invention provide new approaches to determining an optimized parametric model for structure analysis using optical metrology of repeating structures on a semiconductor substrate or wafer. For example, the model parameters correlation can be significantly reduced. As a result, the model is more stable and the number of the floating parameters may be systematically reduced without significantly compromising the model fit.

To provide context, conventionally, parametric models are defined with their geometric and material parameters. Parameter sensitivities are evaluated through simulation. Fixed error analysis is performed to determine a suitable set of parameters to be floated. In many cases, such parameters are highly correlated, which can render the model as unstable and can introduce effects such as toggling. Fixing one or more of the correlated parameters can render the model more stable, but such fixing may introduce significant errors in the final results.

Figure 1A:
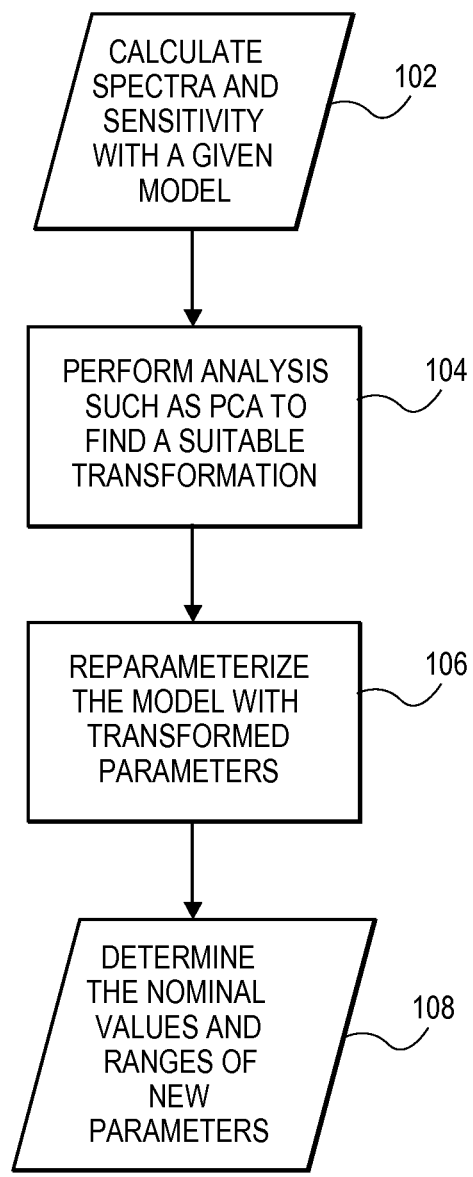
FIG. 1A is a flowchart illustrating representative operations in a method of determining a new parameterization, in accordance with an embodiment of the present invention.

By contrast, FIG. 1A is a flowchart 100 illustrating representative operations in a method of determining a new parameterization, in accordance with an embodiment of the present invention. Referring to flowchart 100, at operation 102, a sensitivity analysis of spectra is performed with respect to the model parameters. At operations 104 and 106, the spectral information is used to determine a new parameterization that minimizes the parameter correlation by transformation. In general, these operations involve working with signals measured as a function of wavelength, polarization, angle, and state of coherence, etc. In a particular embodiment, Principal Components Analysis (PCA) is used, as described in greater detail below. At operation 108, the new model parameter nominal values and ranges are defined and the old parameters are constrained as function of the new parameters.

As mentioned above, the method of flowchart 100 may include use PCA parameterization. The use of PCA for sensitivity analysis may be different for each point of the parameter space. A first exemplary case involves performing PCA on the nominal, and ignoring the errors/correlations for different points in parameter space. A second exemplary case involves performing PCA using data from all multiple points in parameter space (e.g., using standard or detailed analysis from AcuShape). The values are averaged and then sensitivities are collected from all points and PCA is applied on the entire dataset. A third exemplary case involves performing PCA as calculated in real time during regression and library searching. In such an approach, the local space is sampled during each step of the regression. A global model of the parameterization is then generated as a function of geometric parameters.

In an embodiment a parameterization model is obtained by calculating a PCA parameterization for each sample point in a parameter space. A model is generated for each coefficient in the parameterization equations, where each coefficient is as a function of the geometric parameters. During each operation of the regression, the parameterization is constructed using the parameterization model. In one such embodiment, a neural network model implementation (e.g., (GP1, GP2, GP3, . . . )→(cm1), or (GP1, GP2, GP3, . . . )→(cm1, cm2, cm3, . . . )) is used.

Figure 1B:
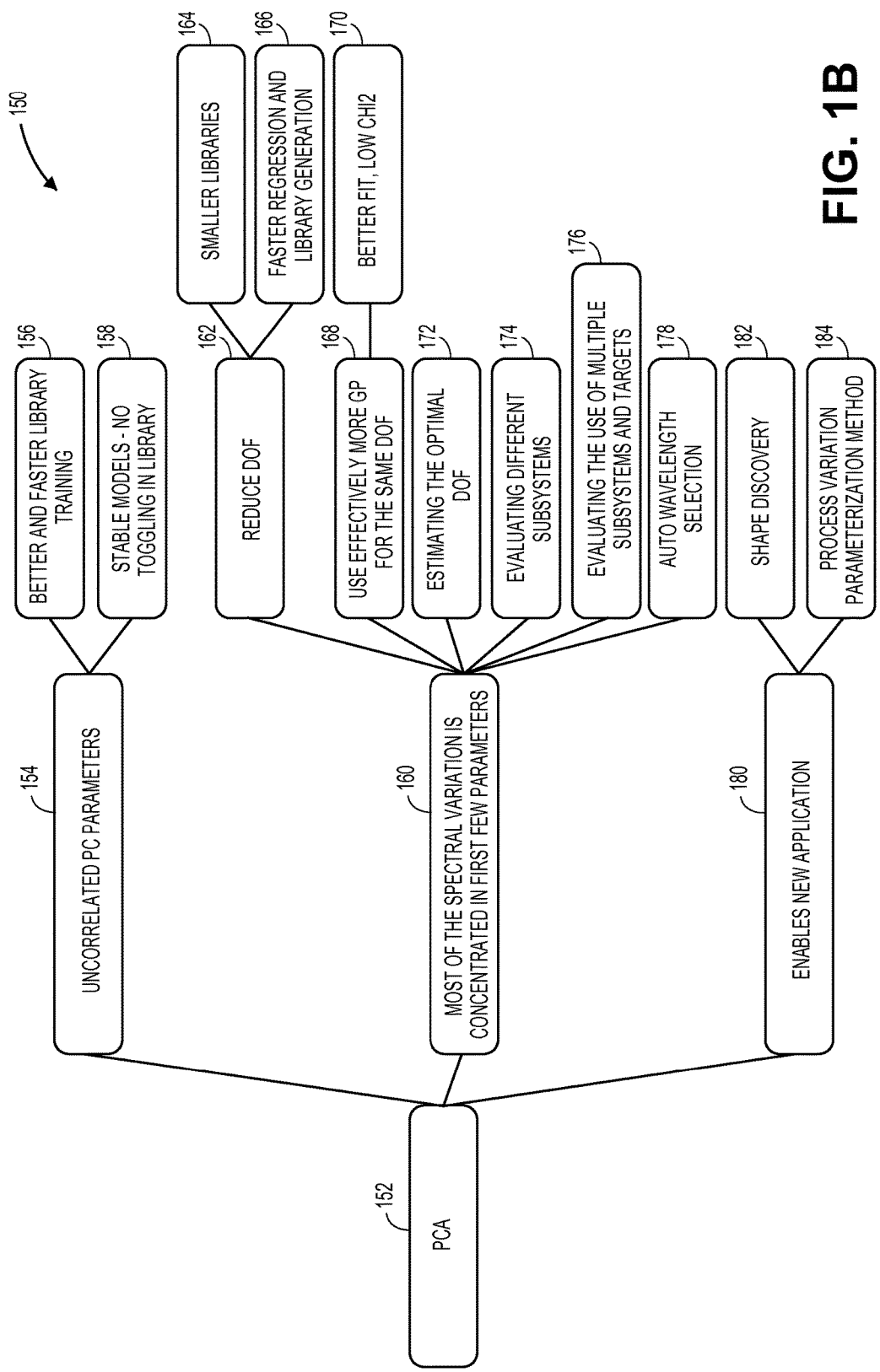
FIG. 1B is a flow diagram illustrating considerations in a Principal Components Analysis (PCA) application, in accordance with an embodiment of the present invention.

FIG. 1B is a flow diagram 150 illustrating considerations in a PCA application, in accordance with an embodiment of the present invention. Referring a flow diagram 150, PCA 152 involves use of uncorrelated principal component (PC) parameters 154. The use of uncorrelated PC parameters 154 can result in better and faster library training 156 and/or stable models with no toggling in the library 158. PCA 152 can also involve concentrating most of the spectral variation in the first few parameters 160. This can result in reduced DOF 162 (e.g., providing smaller libraries 164 and/or faster regression and library generation 166). Also, use effectively more GP for the same DOF 168 can result, e.g., to provide a better fit, low chi2 170. Furthermore, the optimal DOF may be estimated 172, different subsystems can be evaluated 174, the use of multiple subsystems and targets can be evaluated 176, and/or auto wavelength selection can be performed 178. The PCA approach can also involve or enable new applications 180, such as shape discovery 182 and/or process variation parameterization approaches 184.

In another embodiment, approaches described herein involve prediction of the DoF needed for modeling a particular structure. In one such embodiment, two approaches are defined for non-geometric parameterization: PCA and Function+Delta. The Function+Delta type of parameterization may be applied to linear and non-liner parameter correlation. Modeled parameter space reduction (e.g., library size reduction) may be achieved for liner and non-linear parameter spaces in this way. As a result, one or more of the approaches described herein may be used to improve corresponding sensitivity and correlation analysis results.

Figure 2:
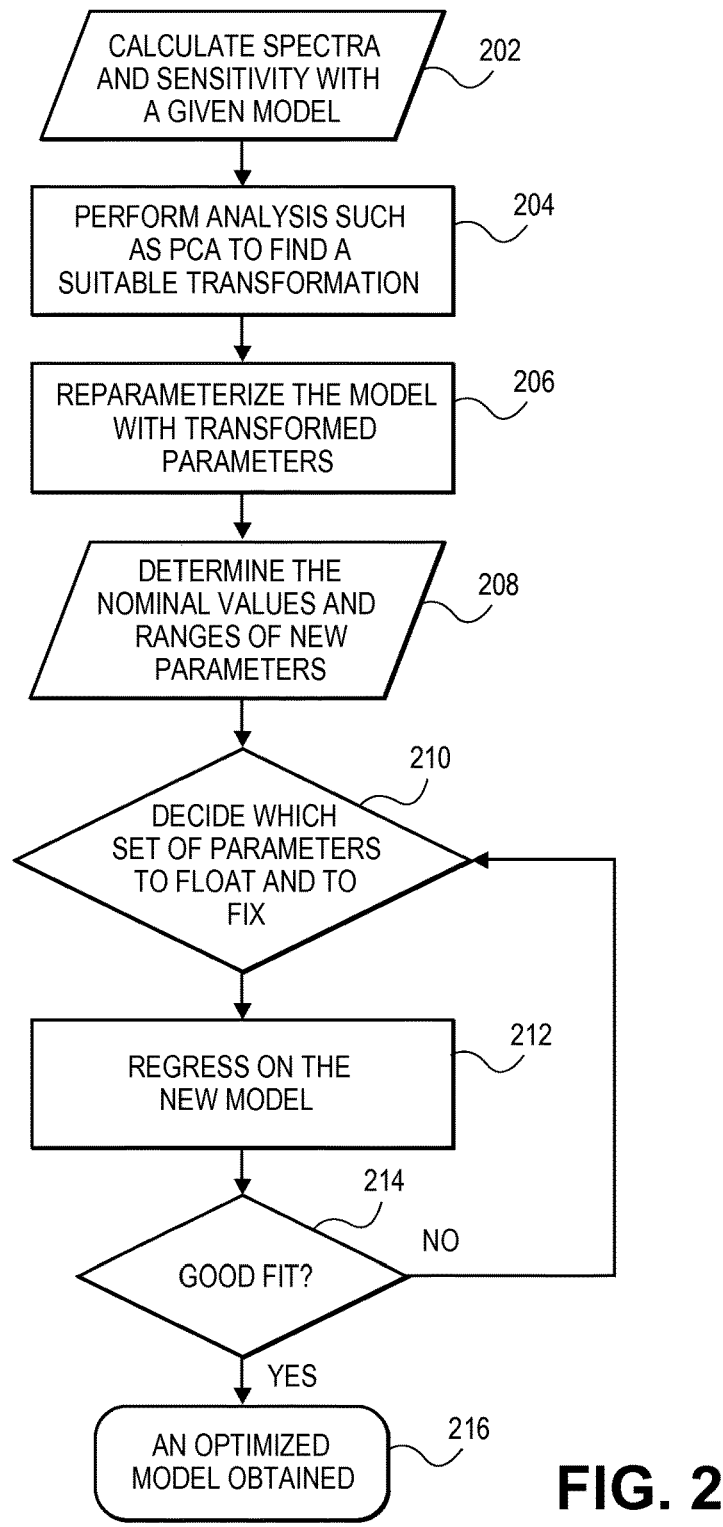
FIG. 2 is a flowchart illustrating representative operations in a method of determining a new parameterization, e.g., for determining an optimized model, in accordance with an embodiment of the present invention.

The above described approaches can be implemented in more complicated procedures. For example, FIG. 2 is a flowchart 200 illustrating representative operations in a method of determining a new parameterization, e.g., for determining an optimized model, in accordance with an embodiment of the present invention. Referring to flowchart 200, at operation 202, spectra and corresponding sensitivity are calculated using a given model. At operation 204, analysis such as PCA is performed to determine a suitable transformation. At operation 206, the model is reparameterized with the transformed parameters and, at operation 208, the nominal values and ranges of the new parameters are determined. At operation 210, a decision is made as to which set of parameters to float and which to fix. At operation 212, regression on the new model is performed. At operation 214, if a good fit is achieved, then an optimized model is obtained at 216. Otherwise, operations 210 and 212 are reiterated until a good fit is found.

Advantages of the approaches described above can include, but are not limited to, elimination or significant reduction of the parameter correlation, as described in greater detail below in association with FIG. 4. For example, there are a number of benefits of reducing parameter correlation in a model such as (1) redundant parameters are eliminated, thereby reducing the dimensionality of the problem, and permitting smaller library sizes, and faster library and regression calculations, and (2) numerical instabilities are reduced, which can help mitigate against the model fitting algorithm finding several competing shape solutions with approximately the same fit quality (e.g., mitigate the likelihood of including the correct shape as well as incorrect shapes). Another advantage is that the new parameters are ordered naturally by decreasing sensitivity, allowing straight forward application of the existing best known methods (BKM). Another advantage includes that ability to provide an improved method for estimating the minimal number of degrees of freedom (DOF), as is described in greater detail below in association with FIG. 5.

Figure 6:
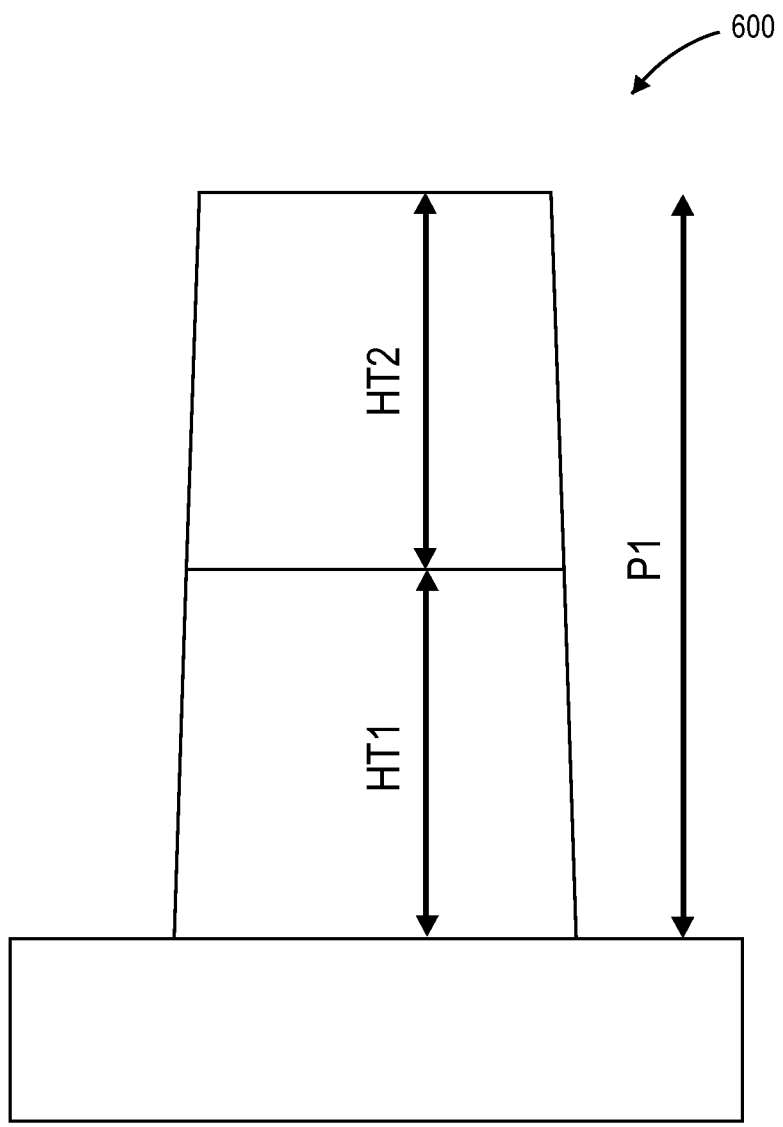
FIG. 6 illustrates a model having floated parameters HT1 and HT2, in accordance with an embodiment of the present invention.

Additional advantages can include the ability to provide a more efficient method of improving the model fit for the same number of model parameters. Also; a more robust way of optimizing model may be provided, e.g., as described in greater detail below, FIG. 6 shows a model in which the floated parameters HT1 and HT2 are highly correlated and have high sensitivity. Other advantages can include the ability to effectively float more parameters of the original model to create opportunities for better model fit. For example, a 5 DOF PCA parameters model constructed from 10 DOF geometric parameter model may have better fit than a 5 DOF geometric parameters model. This can improve the model stability. Another advantage can include reducing library size and regression toggling effects. Essentially, the library to regression matching is improved. Other advantages to the above described approaches can include the ability to reduce the library size (e.g., by reducing the DOF), improving the library construction (e.g., due to the use of uncorrelated parameters). Furthermore, the analysis, regression and library generation times may be reduced (e.g., by reducing the DOF), and characterization of process variations can be improved. It is to be understood that, in one embodiment, a library is defined as a reduced model of the original function or mathematical model such that the evaluation for the function/mathematical model with a library is fast but the resulting values are closely approximate the original values.

Figure 3:
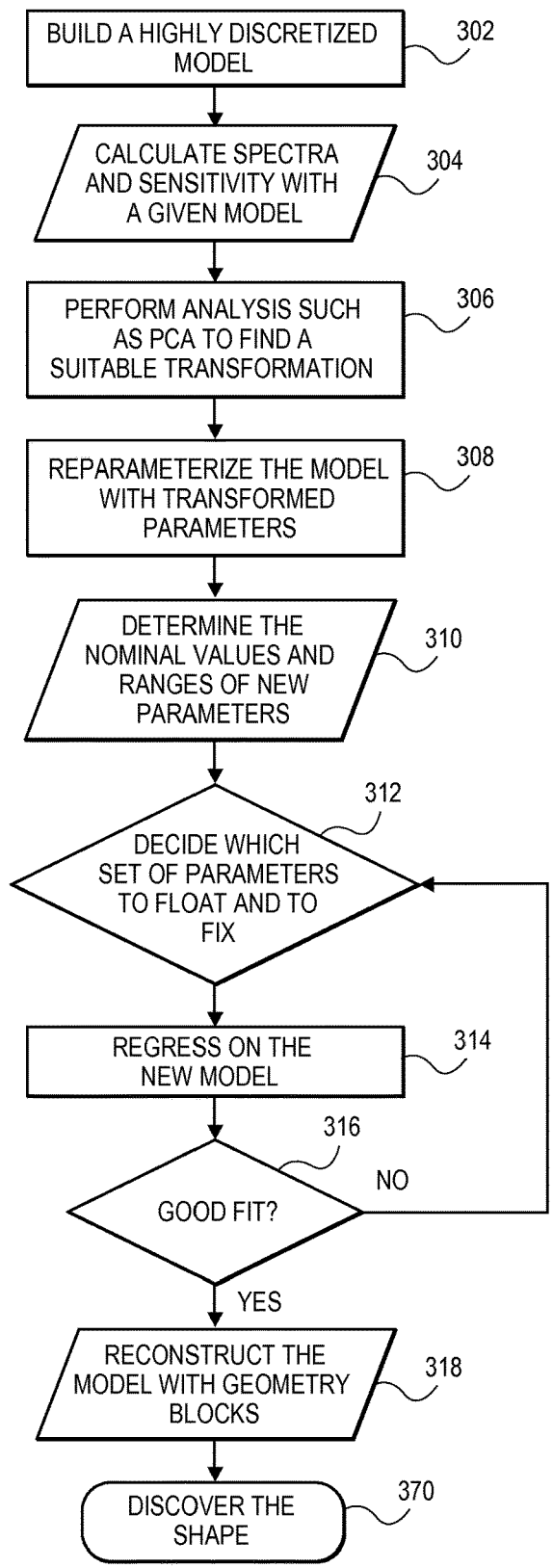
FIG. 3 is a flowchart illustrating representative operations in another method of determining a new parameterization, in accordance with an embodiment of the present invention.

In an embodiment, using an above described approach to modeling, the use of high DOF discretized models for shape discovery is enabled. This allows for determining a complex shape by using a highly discretized but simple initial model. As an example, FIG. 3 is a flowchart 300 illustrating representative operations in another method of determining a new parameterization, in accordance with an embodiment of the present invention. Referring to flowchart 300, at operation 302, a highly discretized model is constructed. At operation 304, spectra and ray sensitivities are calculated and, then, PCA is performed at operation 306. The new PCA parameterization is performed at operations 308 and 310. The degrees of freedom (DoF) are then reduced at operation 312. A regression is run at operation 314 to discover the shape and shape changes over the process space. The resulting model, if a good fit 316 is used as is or is simplified by using appropriate features (e.g., bow, top or rounding features) at operations 318 and 320. If not a good fit, operations 312 and 314 can be reiterated until a good fit is found.

Figure 4:
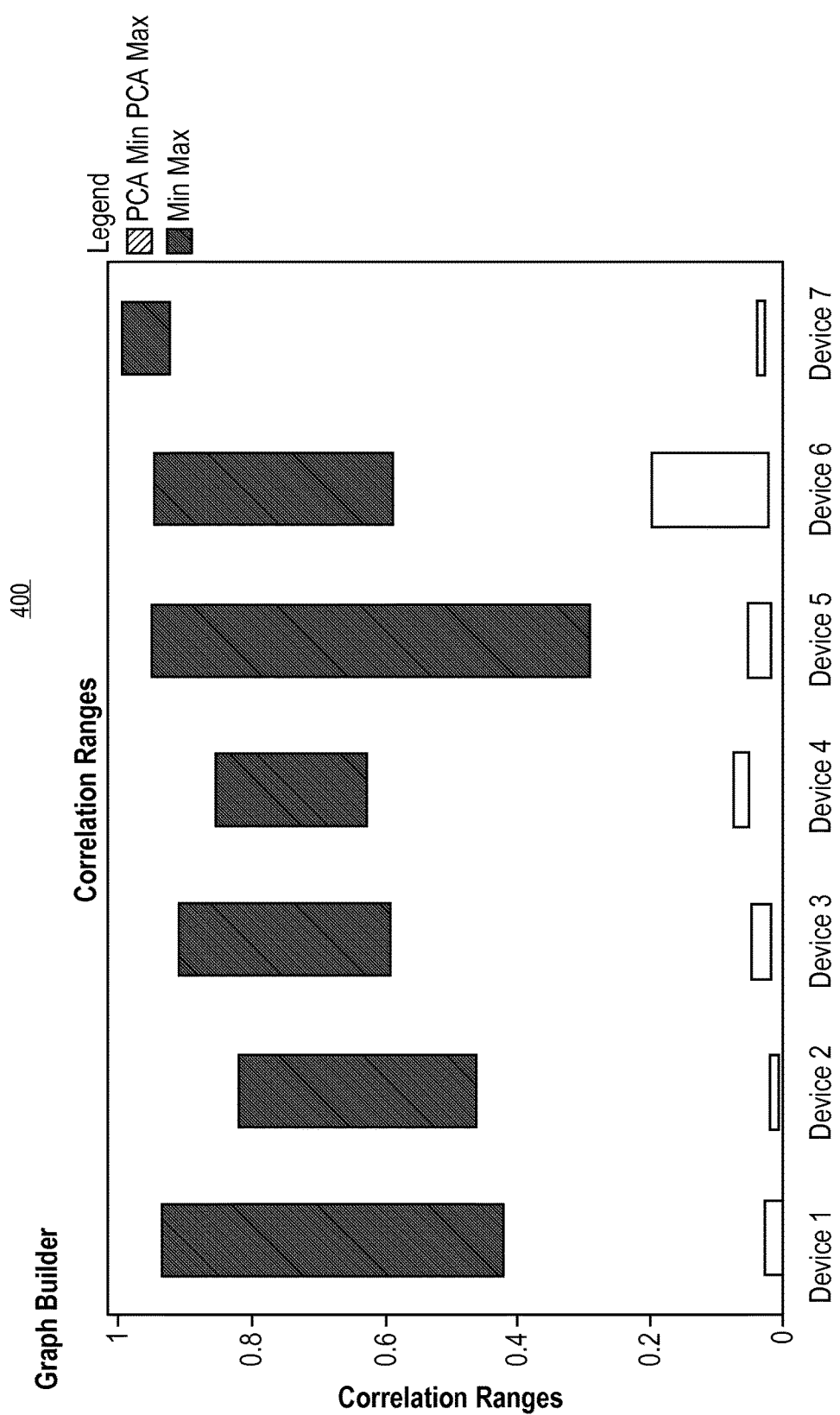
FIG. 4 is a plot of correlation ranges as a function of Devices 1-7 showing PCAmin and PCAmax ranges and associated min/max ranges, in accordance with an embodiment of the present invention.

FIG. 4 is a plot 400 of correlation ranges as a function of Devices 1-7 showing PCAmin and PCAmax ranges and associated min/max ranges, in accordance with an embodiment of the present invention. Referring to plot 400, elimination or significant reduction of the parameter correlation can be achieved using spectral sensitivity analysis during PCA calculations.

Figure 5:
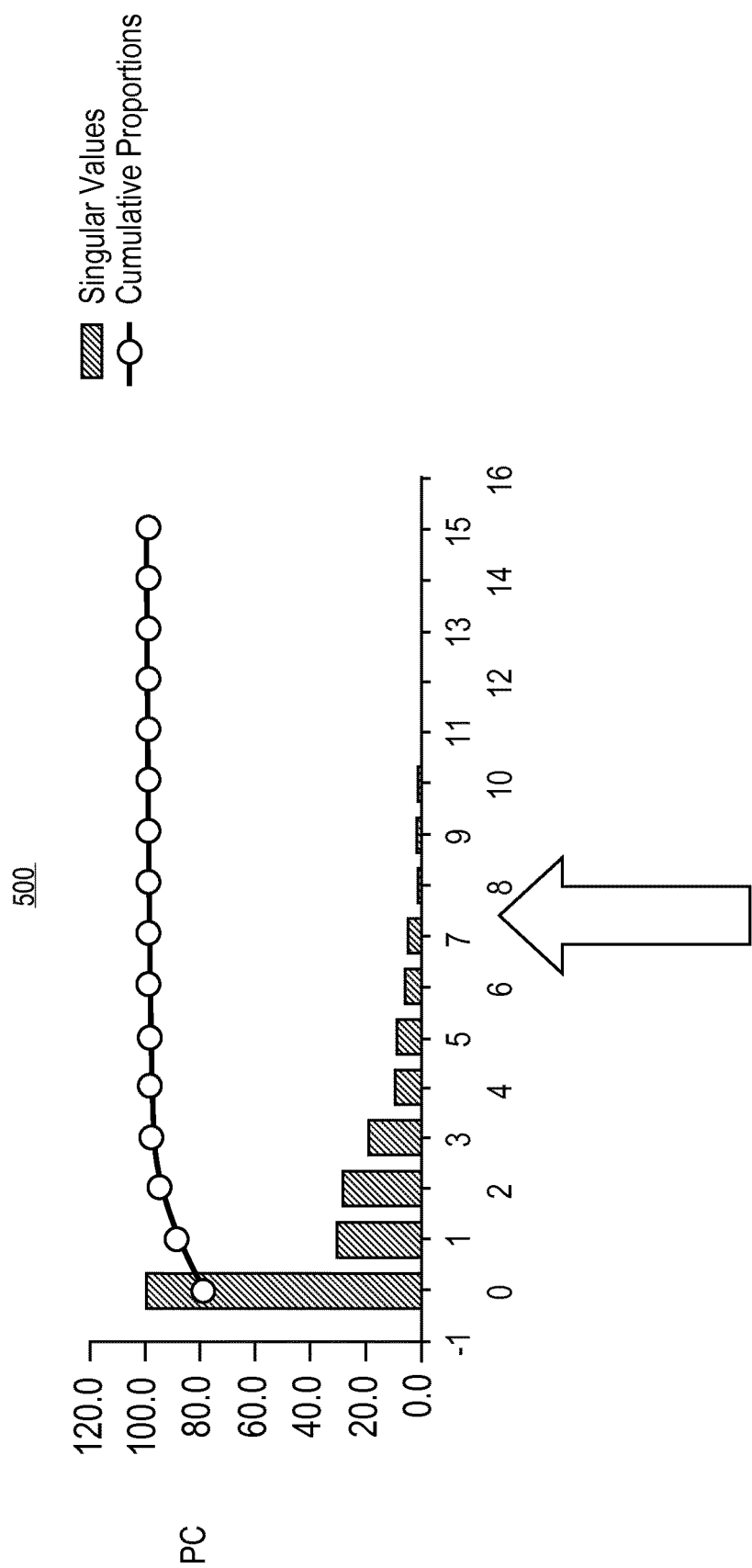
FIG. 5 is a plot of principal components as a function of degrees of freedom (DOF) for a principal component analysis (PCA), with both singular values and cumulative proportions shown, in accordance with an embodiment of the present invention.

FIG. 5 is a plot 500 of principal components as a function of degrees of freedom (DOF) for a principal component analysis (PCA), with both singular values and cumulative proportions shown, in accordance with an embodiment of the present invention. Referring to plot 500, approximately 8 DoF are needed in this example. Using more will likely lead to model instability, while using less will not capture all spectral sensitivity. Thus, the minimal number of degrees of freedom (DOF) for good model fit may be estimated.

FIG. 6 illustrates a model 600 having floated parameters HT1 and HT2, in accordance with an embodiment of the present invention. Referring to model 600, the floated parameters HT1 and HT2 are highly correlated and have high sensitivity. The model will initially fail due to numerical instability. However, after changing of the parameterization, the new model allows both heights to vary in a controlled way through the new parameter P1. Thus, a more robust way of optimizing model is provided.

Overall and more generally, in an embodiment, determining the new spectral sensitivity based parameterization and old/new model parameters relations can be performed in one or more of the following ways: (1) performing PCA, Independent Component Analysis (ICA), or Detrended Correspondence Analysis (DCA), (2) performing non-linear methods such as Auto-Associative Neural Networks (AANN), PCA-ANN, or kernel PCA, (3) searching in the parameterization space using genetic algorithms and genetic programming to find the constraint equations, (4) performing the methods above and adding/modifying custom user defined equation, (5) performing the methods above by using the combined spectra sensitivity data obtained from multiple points in parameter space, (6) performing the methods above by using the combined spectra sensitivity data obtained from multiple rays (e.g., Azimuth (Az), Angle of Incidence (AOI), and Polarization State), (7) adaptively changing the parameterization based on the current point in parameter space of the process variation ranges, (8) fitting/optimizing the transformation coefficients so that correlation is minimized or close to minimized, and/or (9) performing one of the above-mentioned techniques as applied to a sensitivity matrix, its close approximation, or a function of the sensitivity matrix such as a diagonal scaling of the sensitivity matrix.

In an embodiment, one or more of the above described approaches can be implemented for selecting the most capable metrology subsystem or a combination of subsystems. As an example, spectroscopic ellipsometry (SE) can be performed at an AOI of approximately 70 degrees, or a combination of SE and angle-resolved reflectometry, or X-ray metrology such as SAXS, or electron beam approaches can be used. The approach involves running PCA on different subsystems and evaluating the number or PCA parameters that can be reliably measured by different metrology subsystems or combinations of subsystems.

In an embodiment, one or more of the above described approaches can be performed using a geometric model (e.g., using critical dimension (CD) or film thickness values), material parameters (e.g., using n&k, composition, or density values), system parameters (e.g., using AOI, Azimuth angle, wavelength, diffracted angle, polarizer angle values), or combinations thereof. Approaches described herein can also be used to optimize metrology with multiple targets (and/or with multiple tools), such as those disclosed in U.S. Pat. No. 7,478,019, "Multiple tool and structure analysis," to KLA-Tencor, which is incorporated by reference herein. Additionally, the approaches described herein can be used on multiple sets of data using feed-forward, and feed sideways, and simultaneous analysis. In a particular embodiment, one or more of the above approaches is applied on a subset of the parameters in play.

General advantages to the above described spectral sensitivity approaches include significant simplification of the decision making process of an applications engineer by eliminating multiple parameter correlation from high degree of freedom models. Also, a more compact parameterization is provided. Furthermore, more stable regression and library performance is provided, resulting in high quality and rapid applications solutions.

Figure 7:
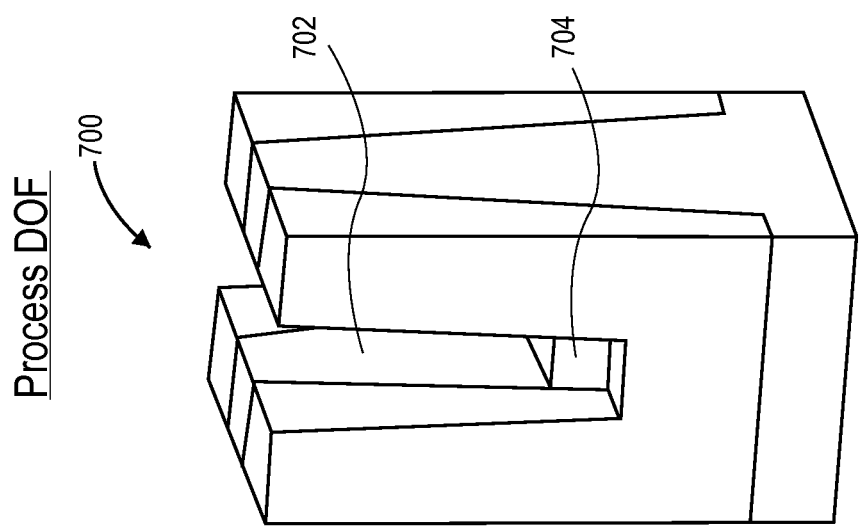
FIG. 7 illustrates an angled view of a double cross-section of a semiconductor structure fabricated by a process methodology, in accordance with an embodiment of the present invention.

As described above, one or more embodiments of the present invention may be directed toward improving a model, such as an optical model. As an example of one of many possible re-parameterizations contemplated within the spirit and scope of embodiments of the present invention, parameters of a three-dimensional structure may be selected for modeling purposes. FIG. 7 illustrates an angled view of a double cross-section of a semiconductor structure 700 fabricated by a process methodology, in accordance with an embodiment of the present invention. As an example, semiconductor structure has an etch feature 702 and internal topography 704 within the etch feature 702. As a consequence of the process used to fabricate semiconductor structure 700, such as an etch process, realistically there is only a subset of options for the overall shape and detailed features of the structure.

Figure 8:
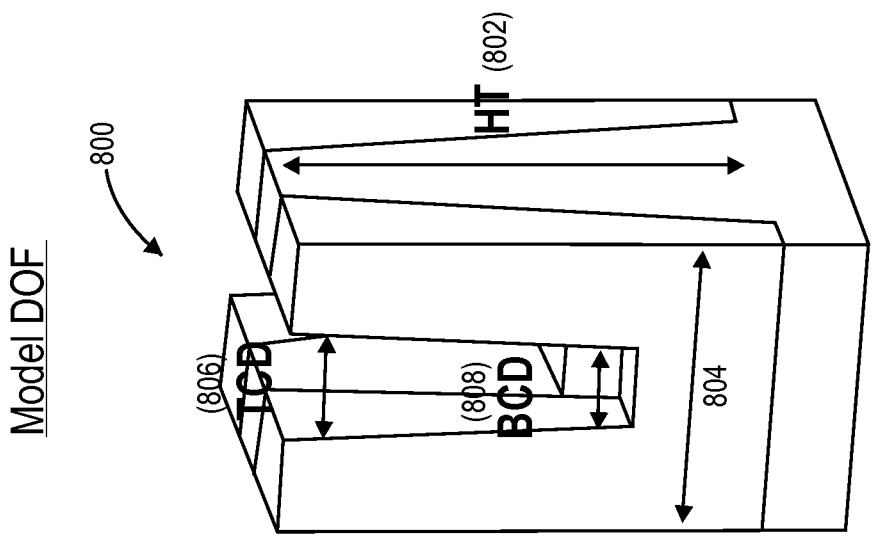
FIG. 8 illustrates an angled view of a double cross-section of a semiconductor structure model which may be used to model the structure of FIG. 7, in accordance with an embodiment of the present invention.

Thus, not every possible combination need be used for modeling such a structure. For example, FIG. 8 illustrates an angled view of a double cross-section of a semiconductor structure model 800 which may be used to model the structure of FIG. 7, in accordance with an embodiment of the present invention. Referring to FIG. 8, since there are finite possible outcomes with respect to fabricating structure 700, the model 800 focuses on a subset of parameters. As a specific, but non-limiting example, structure height (HT) 802, structure width (804), top critical dimension (TCD) 806 and bottom critical dimension (BCD) 808 are shown as possible parameters that may be analyzed in a modeling process. Thus, although process variations will inevitably change the geometry of a resulting structure, multiple features may be affected in a similar way. That is, the parameters may be viewed as correlated. Process DOF is the number of independent variations. The user decides how many parameters to float. Model DOF is the number of geometric parameters that user selected to float.

Figure 9:
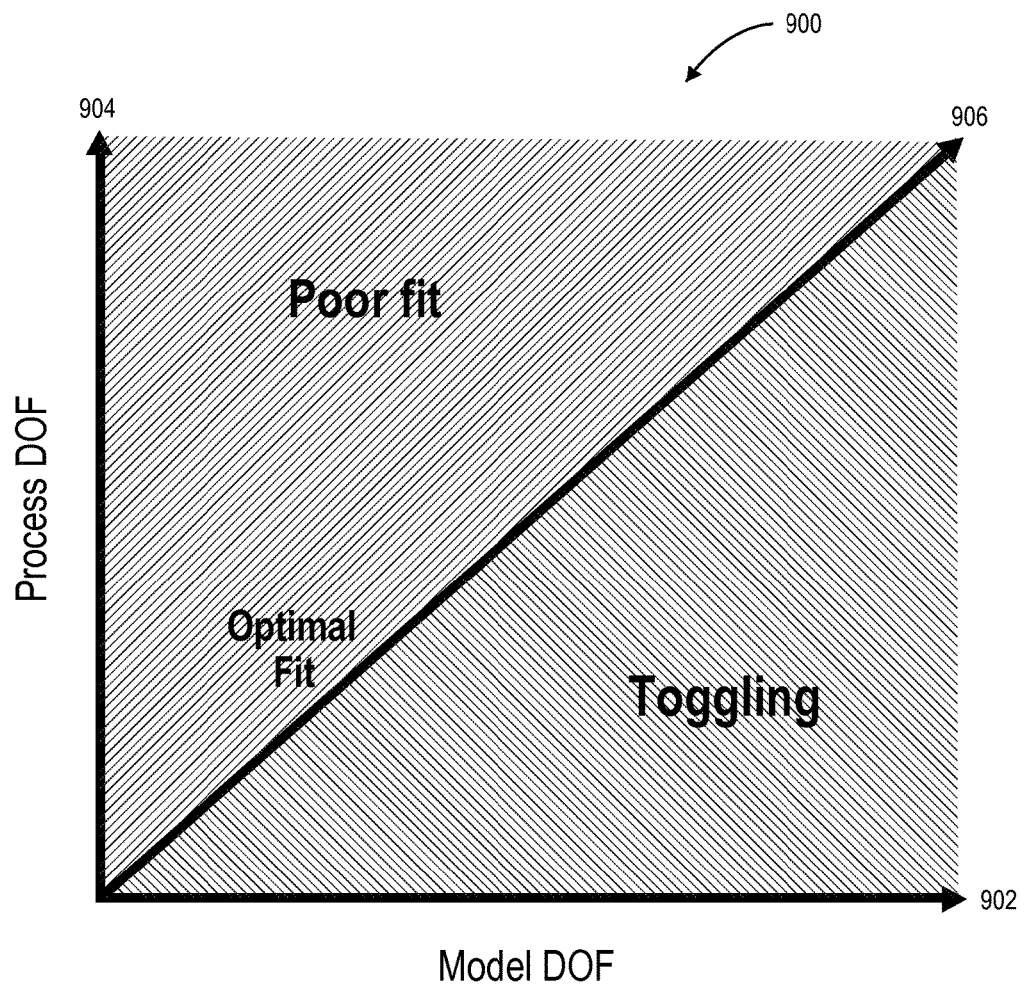
FIG. 9 is a plot of model DOF along a first axis, process DOF along a second orthogonal axis, and an optimal fit axis located between the first and second axis, in accordance with an embodiment of the present invention.

To further illustrate the relationship between process DOF and model DOF, FIG. 9 is a plot 900 of model DOF along a first axis 902, process DOF along a second orthogonal axis 904, and an optimal fit axis 906 located between the first and second axis, in accordance with an embodiment of the present invention. Referring to plot 900, in the space overly proximate to the process DOF axis 904, a poor modeling fit is achieved. For example, certain features may not be modeled or are underdefined. By contrast, in the space overly proximate to the model DOF axis 902, toggling may result. For example, there may be multiple minima or feature parameters may be overdefined in this space. Accordingly, the optimal fit 906 is not overly proximate to either of axes 902 or 904.

It is to be understood that approaches described above can involve providing a simulated spectrum derived from an optimized model of a structure. In an embodiment, further to that, the approaches can further include comparing the simulated spectrum to a sample spectrum derived from the structure. Embodiments describing approaches of performing such operations are described in greater detail below.

In general, orders of a diffraction signal may be simulated as being derived from a periodic structure. The zeroth order represents a diffracted signal at an angle equal to the angle of incidence of a hypothetical incident beam, with respect to the normal N of the periodic structure. Higher diffraction orders are designated as +1, +2, +3, −1, −2, −3, etc. Other orders known as evanescent orders may also be considered. In accordance with an embodiment of the present invention, a simulated diffraction signal is generated for use in optical metrology. For example, profile parameters, such as structural shape and film thicknesses, may be modeled for use in optical metrology. Optical properties of materials, such as index of refraction and coefficient of extinction, (n & k), in structures may also be modeled for use in optical metrology.

Figure 10:
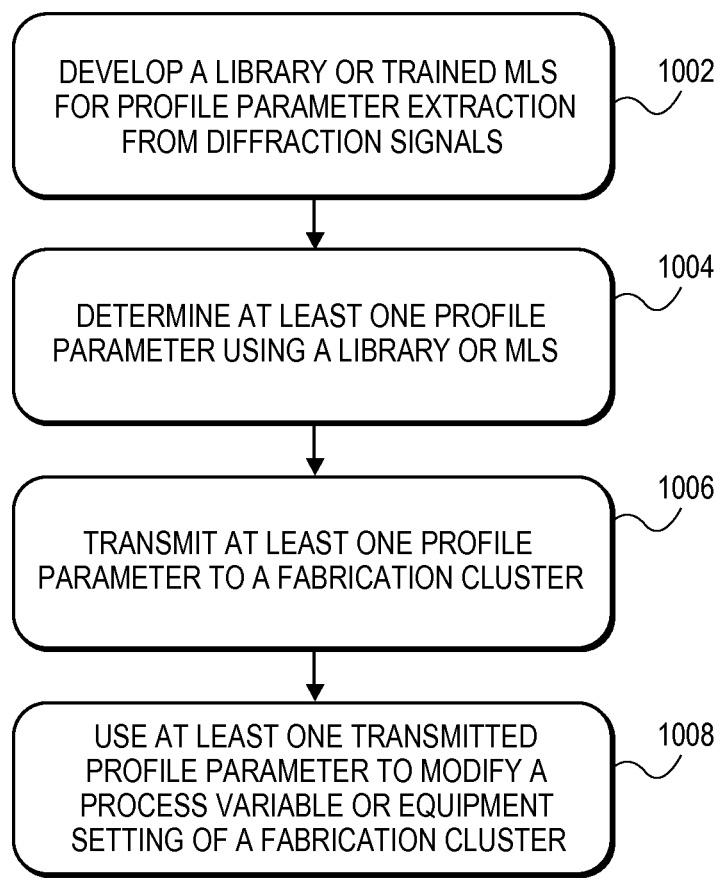
FIG. 10 depicts a flowchart representing an exemplary series of operations for determining and utilizing structural parameters for automated process and equipment control, in accordance with an embodiment of the present invention.

Calculations based simulated diffraction orders may be indicative of profile parameters for a patterned film, such as a patterned semiconductor film or structure based on a stack of films, and may be used for calibrating automated processes or equipment control. FIG. 10 depicts a flowchart 1000 representing an exemplary series of operations for determining and utilizing structural parameters for automated process and equipment control, in accordance with an embodiment of the present invention.

Referring to operation 1002 of flowchart 1000, a library or trained machine learning systems (MLS) is developed to extract parameters from a set of measured diffraction signals. In operation 1004, at least one parameter of a structure is determined using the library or the trained MLS. In operation 1006, the at least one parameter is transmitted to a fabrication cluster configured to perform a processing operation, where the processing operation may be executed in the semiconductor manufacturing process flow either before or after measurement operation 1004 is made. In operation 1008, the at least one transmitted parameter is used to modify a process variable or equipment setting for the processing operation performed by the fabrication cluster.

For a more detailed description of machine learning systems and algorithms, see U.S. Pat. No. 7,831,528, entitled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety. For a description of diffraction order optimization for two-dimensional repeating structures, see U.S. Pat. No. 7,428,060, entitled OPTIMIZATION OF DIFFRACTION ORDER SELECTION FOR TWO-DIMENSIONAL STRUCTURES, filed on Mar. 24, 2006, which is incorporated herein by reference in its entirety.

Figure 11:
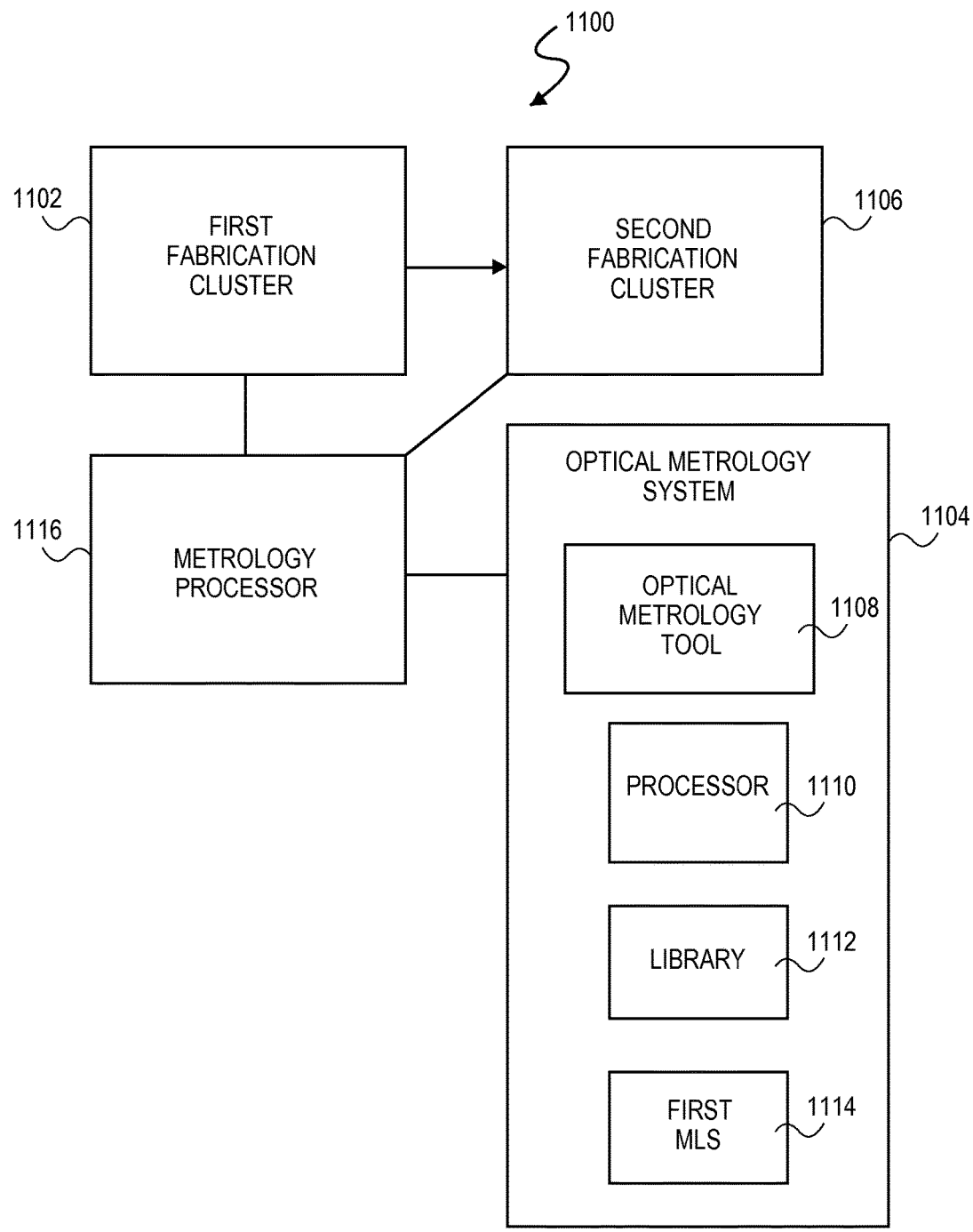
FIG. 11 is an exemplary block diagram of a system for determining and utilizing structural parameters for automated process and equipment control, in accordance with an embodiment of the present invention.

FIG. 11 is an exemplary block diagram of a system 1100 for determining and utilizing structural parameters, such as profile or film thickness parameters, for automated process and equipment control, in accordance with an embodiment of the present invention. System 1100 includes a first fabrication cluster 1102 and optical metrology system 1104. System 1100 also includes a second fabrication cluster 1106. Although the second fabrication cluster 1106 is depicted in FIG. 11 as being subsequent to first fabrication cluster 1102, it should be recognized that second fabrication cluster 1106 can be located prior to first fabrication cluster 1102 in system 1100 (and, e.g., in the manufacturing process flow).

In one exemplary embodiment, optical metrology system 1104 includes an optical metrology tool 1108 and processor 1110. Optical metrology tool 1108 is configured to measure a diffraction signal obtained from the structure. If the measured diffraction signal and the simulated diffraction signal match, one or more values of the profile or film thickness parameters are determined to be the one or more values of the profile or film thickness parameters associated with the simulated diffraction signal.

In one exemplary embodiment, optical metrology system 1104 can also include a library 1112 with a plurality of simulated diffraction signals and a plurality of values of, e.g., one or more profile or film thickness parameters associated with the plurality of simulated diffraction signals. As described above, the library can be generated in advance. Metrology processor 1110 can be used to compare a measured diffraction signal obtained from a structure to the plurality of simulated diffraction signals in the library. When a matching simulated diffraction signal is found, the one or more values of the profile or film thickness parameters associated with the matching simulated diffraction signal in the library is assumed to be the one or more values of the profile or film thickness parameters used in the wafer application to fabricate the structure.

System 1100 also includes a metrology processor 1116. In one exemplary embodiment, processor 1110 can transmit the one or more values of the, e.g., one or more profile or film thickness parameters to metrology processor 1116. Metrology processor 1116 can then adjust one or more process parameters or equipment settings of first fabrication cluster 1102 based on the one or more values of the one or more profile or film thickness parameters determined using optical metrology system 1104. Metrology processor 1116 can also adjust one or more process parameters or equipment settings of the second fabrication cluster 1106 based on the one or more values of the one or more profile or film thickness parameters determined using optical metrology system 1104. As noted above, fabrication cluster 1106 can process the wafer before or after fabrication cluster 1102. In another exemplary embodiment, processor 1110 is configured to train machine learning system 1114 using the set of measured diffraction signals as inputs to machine learning system 1114 and profile or film thickness parameters as the expected outputs of machine learning system 1114.

Figure 12A:
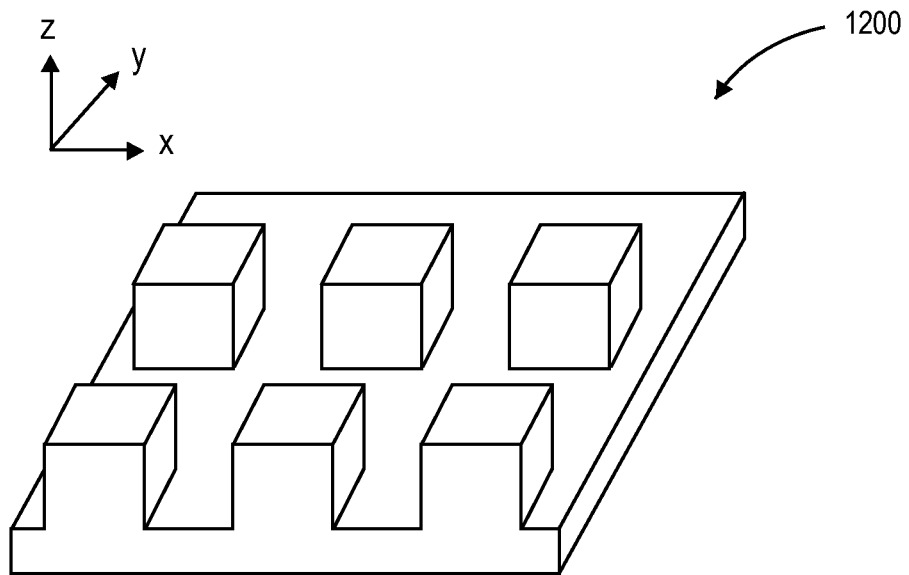
FIG. 12A depicts a periodic grating having a profile that varies in the x-y plane, in accordance with an embodiment of the present invention.

In an embodiment, optimizing a model of a structure includes using a three-dimensional grating structure. The term "three-dimensional grating structure" is used herein to refer to a structure having an x-y profile that varies in two horizontal dimensions in addition to a depth in the z-direction. For example, FIG. 12A depicts a periodic grating 1200 having a profile that varies in the x-y plane, in accordance with an embodiment of the present invention. The profile of the periodic grating varies in the z-direction as a function of the x-y profile.

Figure 12B:
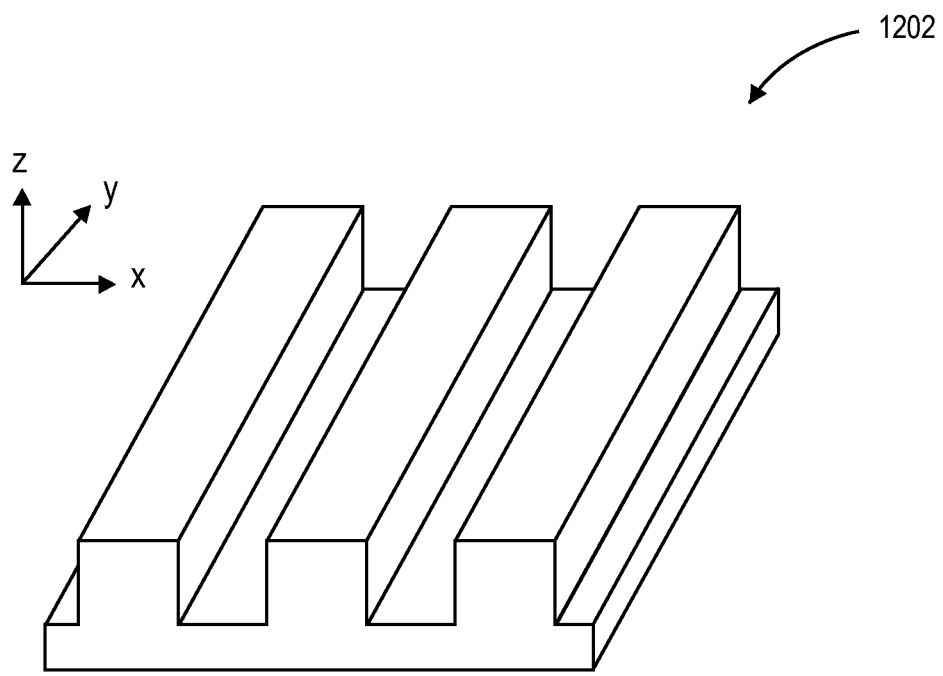
FIG. 12B depicts a periodic grating having a profile that varies in the x-direction but not in the y-direction, in accordance with an embodiment of the present invention.

In an embodiment, optimizing a model of a structure includes using a two-dimensional grating structure. The term "two-dimensional grating structure" is used herein to refer to a structure having an x-y profile that varies in only one horizontal dimension in addition to a depth in the z-direction. For example, FIG. 12B depicts a periodic grating 1202 having a profile that varies in the x-direction but not in the y-direction, in accordance with an embodiment of the present invention. The profile of the periodic grating varies in the z-direction as a function of the x profile. It is to be understood that the lack of variation in the y-direction for a two-dimensional structure need not be infinite, but any breaks in the pattern are considered long range, e.g., any breaks in the pattern in the y-direction are spaced substantially further apart than the breaks in the pattern in the x-direction.

Embodiments of the present invention may be suitable for a variety of film stacks. For example, in an embodiment, a method for optimizing a parameter of a critical dimension (CD) profile or structure is performed for a film stack including an insulating film, a semiconductor film and a metal film formed on a substrate. In an embodiment, the film stack includes a single layer or multiple layers. Also, in an embodiment invention, an analyzed or measured grating structure includes both a three-dimensional component and a two-dimensional component. For example, the efficiency of a computation based on simulated diffraction data may be optimized by taking advantage of the simpler contribution by the two-dimensional component to the overall structure and the diffraction data thereof.

Figure 13:
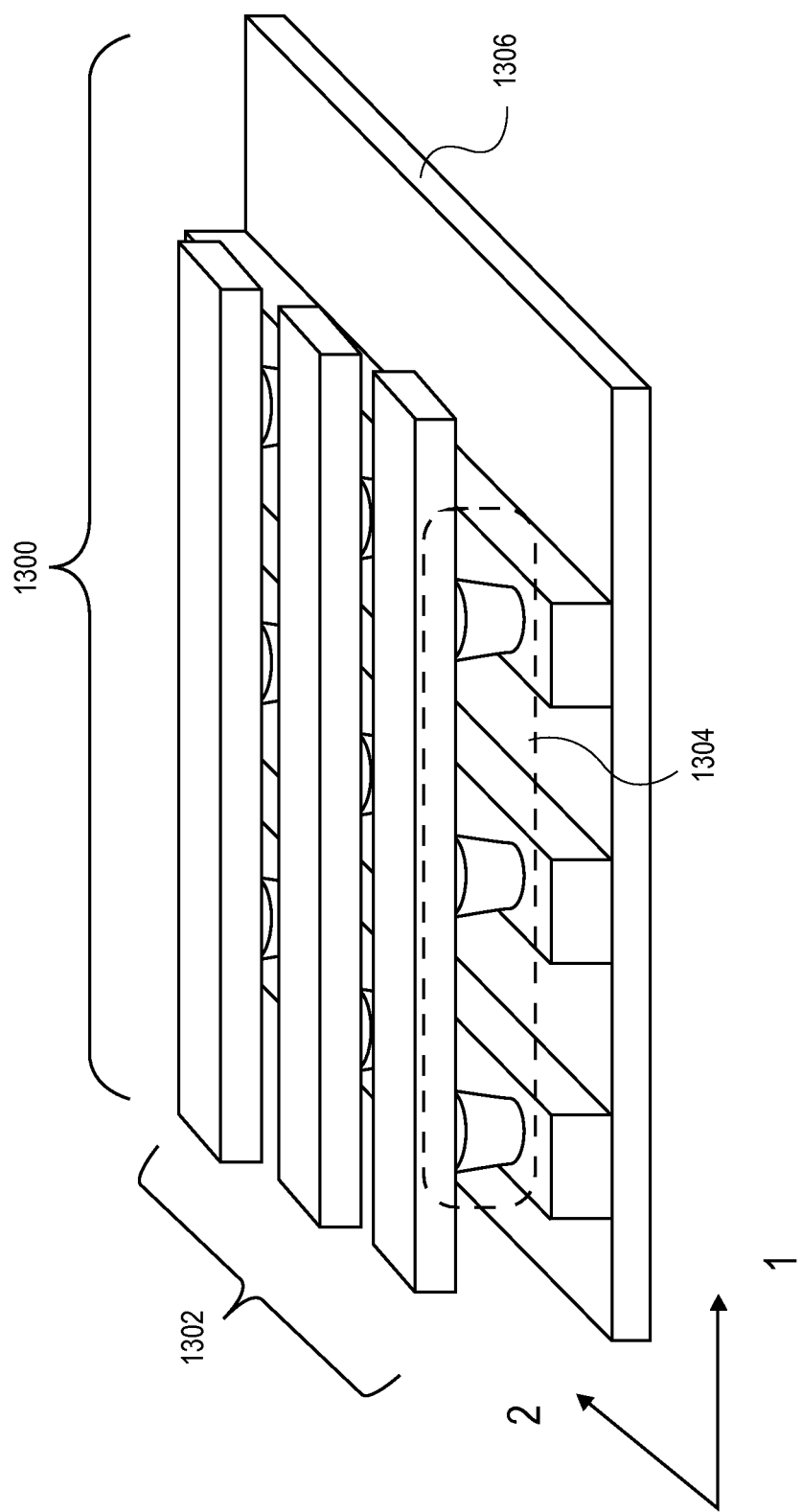
FIG. 13 represents a cross-sectional view of a structure having both a two-dimensional component and a three-dimensional component, in accordance with an embodiment of the present invention.

FIG. 13 represents a cross-sectional view of a structure having both a two-dimensional component and a three-dimensional component, in accordance with an embodiment of the present invention. Referring to FIG. 13, a structure 1300 has a two-dimensional component 1302 and a three-dimensional component 1304 above a substrate 1306. The grating of the two-dimensional component runs along direction 2, while the grating of the three-dimensional component runs along both directions 1 and 2. In one embodiment, direction 1 is orthogonal to direction 2, as depicted in FIG. 13. In another embodiment, direction 1 is non-orthogonal to direction 2.

The above methods may be implemented in an optical critical dimension (OCD) product such as "Acushape" as a utility for an applications engineer to use after initial or preliminary models have been tested. Also, commercially available software such as "COMSOL Multiphysics" may be used to identify regions of an OCD model for alteration. The simulation results from such a software application may be used to predict a region for successful model improvement.

In an embodiment, the method of optimizing a model of a structure further includes altering parameters of a process tool based on an optimized parameter. A concerted altering of the process tool may be performed by using a technique such as, but not limited to, a feedback technique, a feed-forward technique, and an in situ control technique.

In accordance with an embodiment of the present invention, a method of optimizing a model of a structure further includes comparing a simulated spectrum to a sample spectrum. In one embodiment, a set of diffraction orders is simulated to represent diffraction signals from a two- or three-dimensional grating structure generated by an ellipsometric optical metrology system, such as the optical metrology systems 1400 or 1550 described below in association with FIGS. 14 and 15, respectively. However, it is to be understood that the same concepts and principles equally apply to the other optical metrology systems, such as reflectometric systems. The diffraction signals represented may account for features of the two- and three-dimensional grating structure such as, but not limited to, profile, dimension, material composition, or film thickness.

Figure 14:
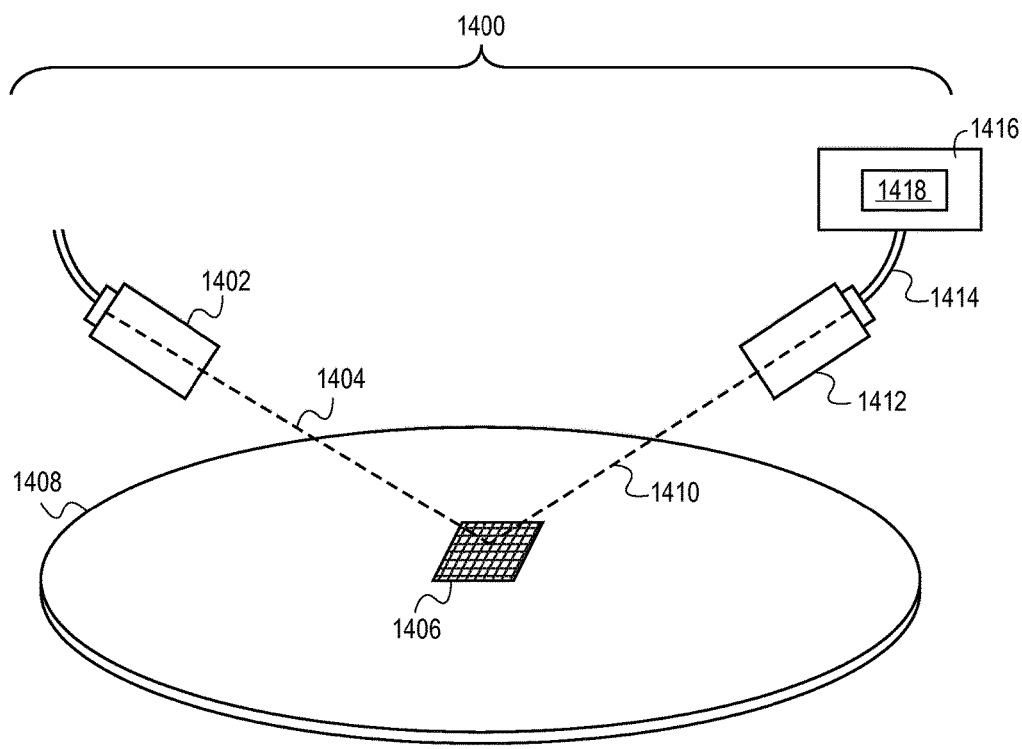
FIG. 14 is a first architectural diagram illustrating the utilization of optical metrology to determine parameters of structures on a semiconductor wafer, in accordance with embodiments of the present invention.

FIG. 14 is an architectural diagram illustrating the utilization of optical metrology to determine parameters of structures on a semiconductor wafer, in accordance with embodiments of the present invention. The optical metrology system 1400 includes a metrology beam source 1402 projecting a metrology beam 1404 at the target structure 1406 of a wafer 1408. The metrology beam 1404 is projected at an incidence angle θ towards the target structure 1406 (θ is the angle between the incident beam 1404 and a normal to the target structure 1406). The ellipsometer may, in one embodiment, use an incidence angle of approximately 60° to 70°, or may use a lower angle (possibly close to 0° or near-normal incidence) or an angle greater than 70° (grazing incidence). The diffraction beam 1410 is measured by a metrology beam receiver 1412. The diffraction beam data 1414 is transmitted to a profile application server 1416. The profile application server 1416 may compare the measured diffraction beam data 1414 against a library 1418 of simulated diffraction beam data representing varying combinations of critical dimensions of the target structure and resolution.

In one exemplary embodiment, the library 1418 instance best matching the measured diffraction beam data 1414 is selected. It is to be understood that although a library of diffraction spectra or signals and associated hypothetical profiles or other parameters is frequently used to illustrate concepts and principles, embodiments of the present invention may apply equally to a data space including simulated diffraction signals and associated sets of profile parameters, such as in regression, neural network, and similar methods used for profile extraction. The hypothetical profile and associated critical dimensions of the selected library 1416 instance is assumed to correspond to the actual cross-sectional profile and critical dimensions of the features of the target structure 1206. The optical metrology system 1400 may utilize a reflectometer, an ellipsometer, or other optical metrology device to measure the diffraction beam or signal.

In order to facilitate the description of embodiments of the present invention, an ellipsometric optical metrology system is used to illustrate the above concepts and principles. It is to be understood that the same concepts and principles apply equally to the other optical metrology systems, such as reflectometric systems. In an embodiment, the optical scatterometry is a technique such as, but not limited to, optical spectroscopic ellipsometry (SE), beam-profile reflectometry (BPR), beam-profile ellipsometry (BPE), and ultra-violet reflectometry (UVR). In a similar manner, a semiconductor wafer may be utilized to illustrate an application of the concept. Again, the methods and processes apply equally to other work pieces that have repeating structures.

Figure 15:
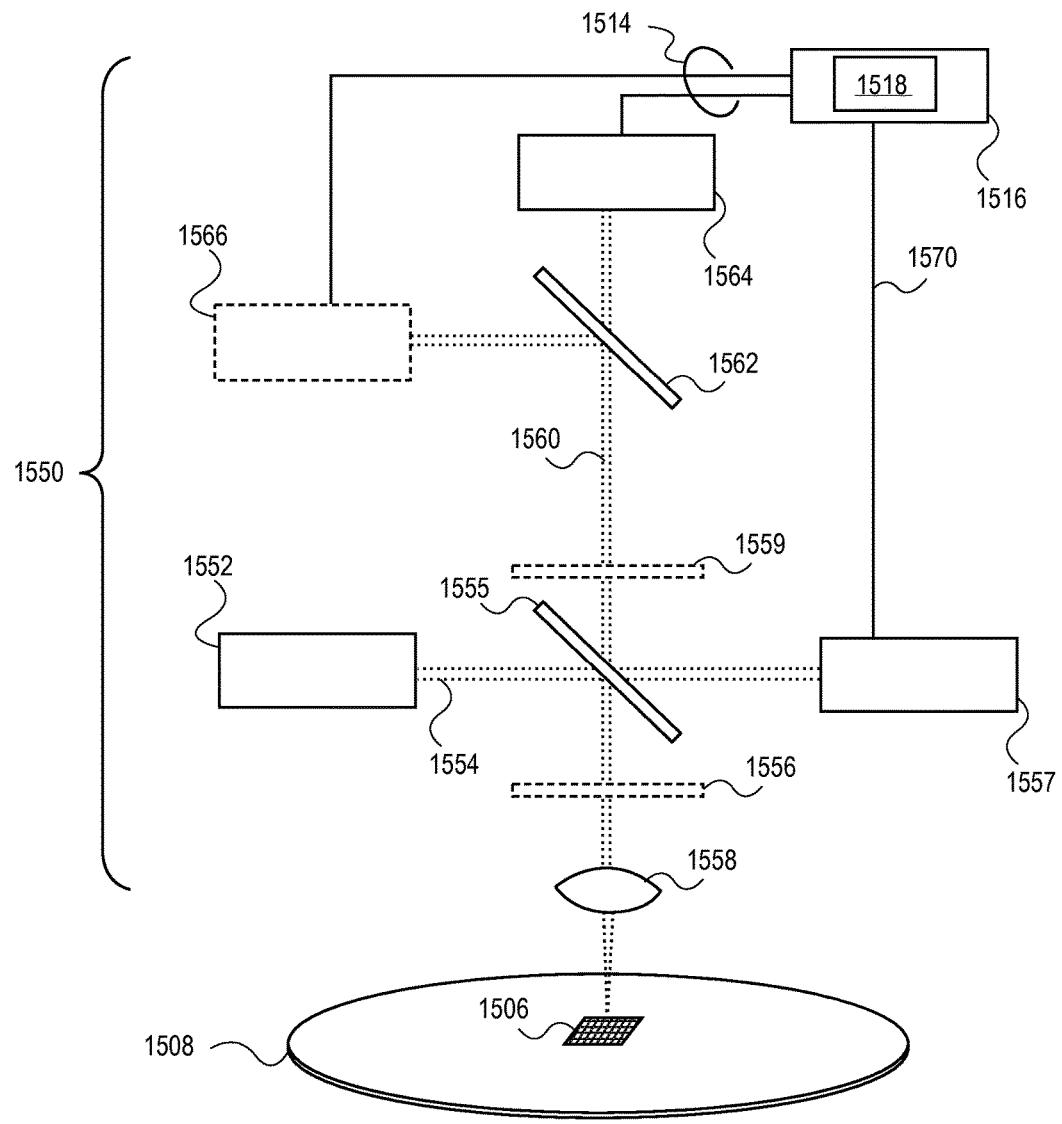
FIG. 15 is a second architectural diagram illustrating the utilization of optical metrology to determine parameters of structures on a semiconductor wafer, in accordance with embodiments of the present invention.

FIG. 15 is an architectural diagram illustrating the utilization of beam-profile reflectometry and/or beam-profile ellipsometry to determine parameters of structures on a semiconductor wafer, in accordance with embodiments of the present invention. The optical metrology system 1550 includes a metrology beam source 1552 generating a polarized metrology beam 1554. Preferably this metrology beam has a narrow bandwidth of 10 nanometers or less. In some embodiments, the source 1552 is capable of outputting beams of different wavelengths by switching filters or by switching between different lasers or super-bright light emitting diodes. Part of this beam is reflected from the beam splitter 1555 and focused onto the target structure 1506 of a wafer 1508 by objective lens 1558, which has a high numerical aperture (NA), preferably an NA of approximately 0.9 or 0.95. The portion of the beam 1554 that is not reflected from the beam splitter is directed to beam intensity monitor 1557. The metrology beam may, optionally, pass through a quarter-wave plate 1556 before the objective lens 1558.

After reflection from the target the reflected beam 1560 passes back through the objective lens and is directed to one or more detectors. If optional quarter-wave plate 1556 is present, the beam will pass back through that quarter-wave plate before being transmitted through the beam splitter 1555. After the beam-splitter, the reflected beam 1560 may optionally pass through a quarter-wave plate at location 1559 as an alternative to location 1556. If the quarter-wave plate is present at location 1556, it will modify both the incident and reflected beams. If it is present at location 1559, it will modify only the reflected beam. In some embodiments, no wave plate may be present at either location, or the wave plate may be switched in and out depending on the measurement to be made. It is to be understood that in some embodiments it might be desirable that the wave plate have a retardance substantially different from a quarter wave, i.e. the retardance value might be substantially greater than, or substantially less than, 90°.

A polarizer or polarizing beam splitter 1562 directs one polarization state of the reflected beam 1560 to detector 1564, and, optionally, directs a different polarization state to an optional second detector 1566. The detectors 1564 and 1566 might be one-dimensional (line) or two-dimensional (array) detectors. Each element of a detector corresponds to a different combination of AOI and azimuthal angles for the corresponding ray reflected from the target. The diffraction beam data 1514 from the detector(s) is transmitted to the profile application server 1516 along with beam intensity data 1570. The profile application server 1516 may compare the measured diffraction beam data 1514 after normalization or correction by the beam intensity data 1570 against a library 1518 of simulated diffraction beam data representing varying combinations of critical dimensions of the target structure and resolution.

For more detailed descriptions of systems that could be used to measure the diffraction beam data or signals for use with the present invention, see U.S. Pat. No. 6,734,967, entitled FOCUSED BEAM SPECTROSCOPIC ELLIPSOMETRY METHOD AND SYSTEM, filed on Feb. 11, 1999, and U.S. Pat. No. 6,278,519 entitled APPARATUS FOR ANALYZING MULTI-LAYER THIN FILM STACKS ON SEMICONDUCTORS, filed Jan. 29, 1998, both of which are incorporated herein by reference in their entirety. These two patents describe metrology systems that may be configured with multiple measurement subsystems, including one or more of a spectroscopic ellipsometer, a single-wavelength ellipsometer, a broadband reflectometer, a DUV reflectometer, a beam-profile reflectometer, and a beam-profile ellipsometer. These measurement subsystems may be used individually, or in combination, to measure the reflected or diffracted beam from films and patterned structures. The signals collected in these measurements may be analyzed to determine parameters of structures on a semiconductor wafer in accordance with embodiments of the present invention.

Embodiments of the present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

Figure 16:
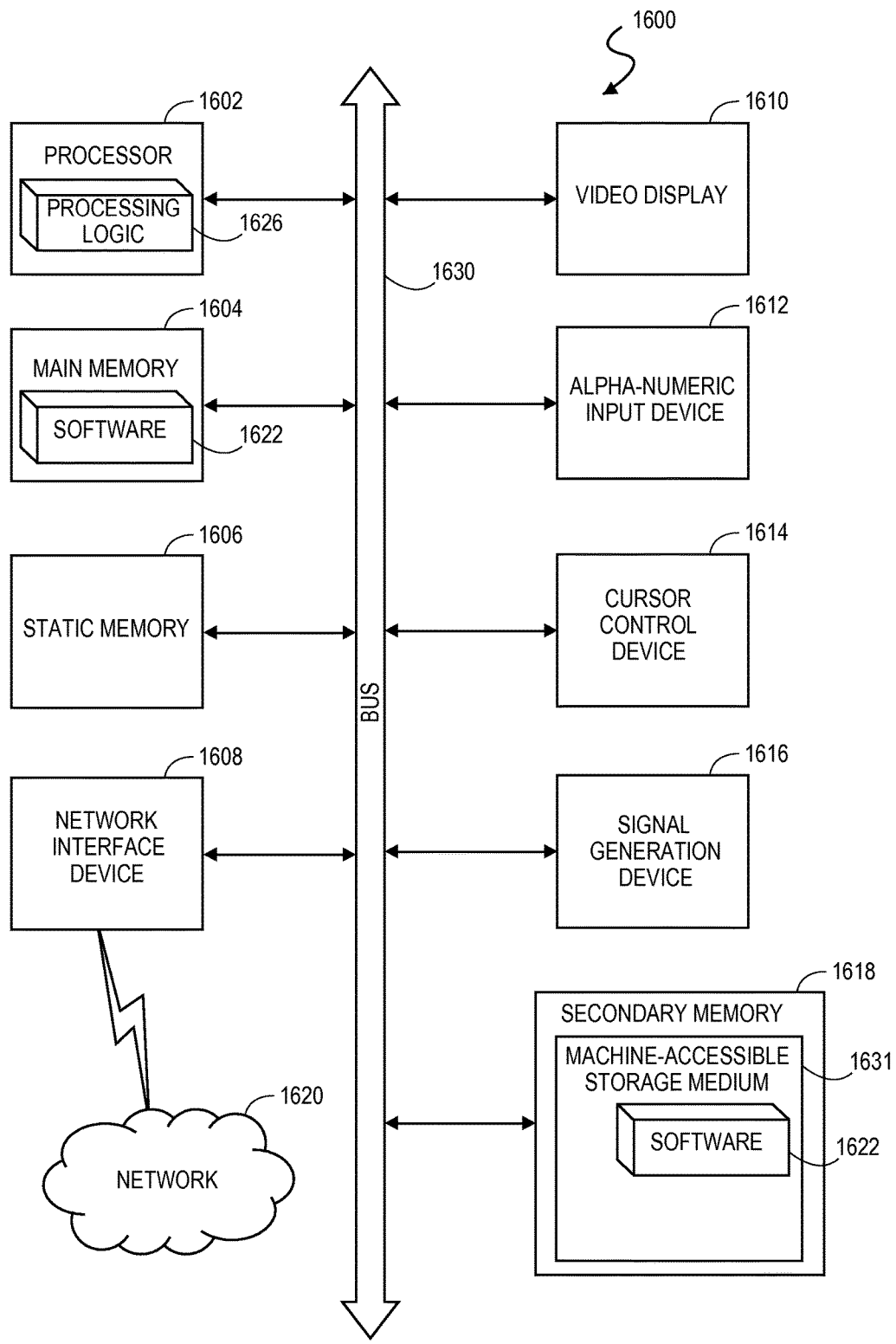
FIG. 16 illustrates a block diagram of an exemplary computer system, in accordance with an embodiment of the present invention.

FIG. 16 illustrates a diagrammatic representation of a machine in the exemplary form of a computer system 1600 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1600 includes a processor 1602, a main memory 1604 (e.g., read-only memory (ROM), flash memory, dynamic random access memory (DRAM) such as synchronous DRAM (SDRAM) or Rambus DRAM (RDRAM), etc.), a static memory 1606 (e.g., flash memory, static random access memory (SRAM), etc.), and a secondary memory 1618 (e.g., a data storage device), which communicate with each other via a bus 1630.

Processor 1602 represents one or more general-purpose processing devices such as a microprocessor, central processing unit, or the like. More particularly, the processor 1602 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1602 may also be one or more special-purpose processing devices such as an application specific integrated circuit (ASIC), a field programmable gate array (FPGA), a digital signal processor (DSP), network processor, or the like. Processor 1602 is configured to execute the processing logic 1626 for performing the operations discussed herein.

The computer system 1600 may further include a network interface device 1608. The computer system 1600 also may include a video display unit 1610 (e.g., a liquid crystal display (LCD) or a cathode ray tube (CRT)), an alphanumeric input device 1612 (e.g., a keyboard), a cursor control device 1614 (e.g., a mouse), and a signal generation device 1616 (e.g., a speaker).

The secondary memory 1618 may include a machine-accessible storage medium (or more specifically a computer-readable storage medium) 1631 on which is stored one or more sets of instructions (e.g., software 1622) embodying any one or more of the methodologies or functions described herein. The software 1622 may also reside, completely or at least partially, within the main memory 1604 and/or within the processor 1602 during execution thereof by the computer system 1600, the main memory 1604 and the processor 1602 also constituting machine-readable storage media. The software 1622 may further be transmitted or received over a network 1620 via the network interface device 1608.

While the machine-accessible storage medium 1631 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media.

In accordance with an embodiment of the present invention, a machine-accessible storage medium has instructions stored thereon which cause a data processing system to perform a method of optimizing parametric models for structural analysis using metrology of repeating structures on a semiconductor substrate or wafer. The method includes determining a first model of a structure. The first model is based on a first set of parameters. A set of spectral sensitivity variations data is determined for the structure. Spectral sensitivity is determined by derivatives of the spectra with respect to the first set of parameters. The first model of the structure is modified to provide a second model of the structure based on the set of spectral sensitivity variations data. The second model of the structure is based on a second set of parameters different from the first set of parameters. A simulated spectrum derived from the second model of the structure is then provided.

It is to be understood that the above methodologies may be applied under a variety of circumstances within the spirit and scope of embodiments of the present invention. For example, in an embodiment, measurements described above are performed with or without the presence of background light. In an embodiment, a method described above is performed in a semiconductor, solar, light-emitting diode (LED), or a related fabrication process. In an embodiment, a method described above is used in a stand-alone or an integrated metrology tool.

Figure 17:
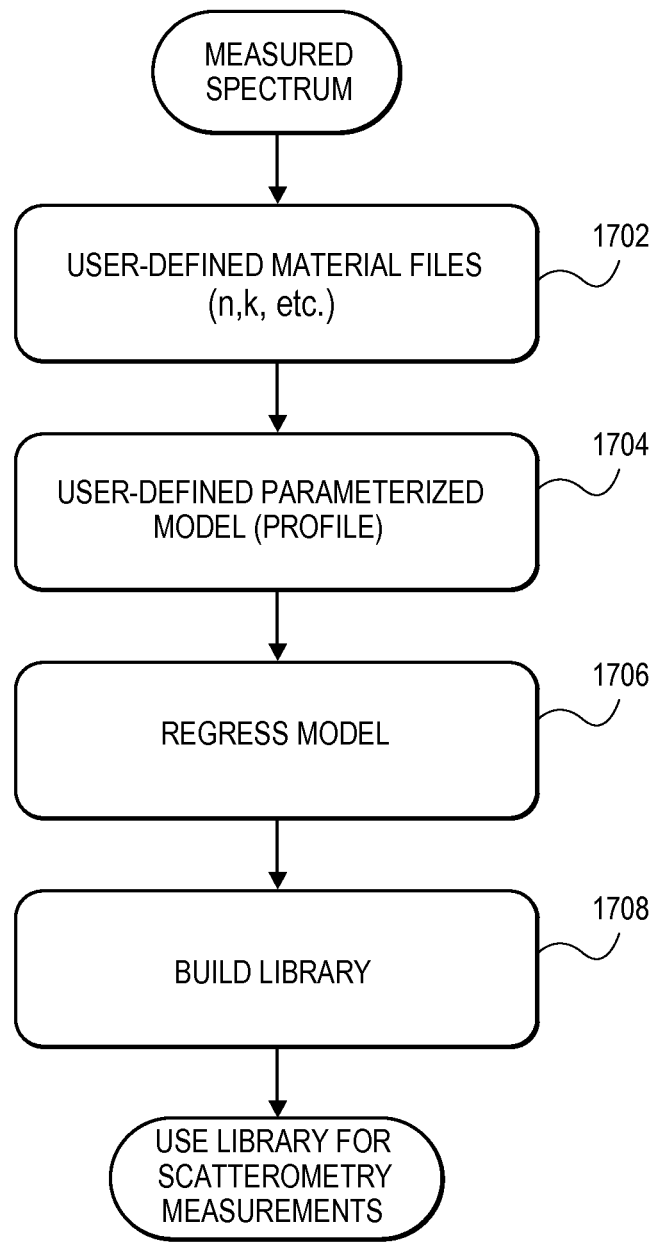
FIG. 17 is a flowchart representing operations in a method for a building parameterized model and a spectral library beginning with sample spectra, in accordance with an embodiment of the present invention.

Analysis of measured spectra generally involves comparing the measured sample spectra to simulated spectra to deduce parameter values of a model that best describe the measured sample. FIG. 17 is a flowchart 1700 representing operations in a method for a building parameterized model and a spectral library beginning with sample spectra (e.g., originating from one or more workpieces), in accordance with an embodiment of the present invention.

At operation 1702, a set of material files are defined by a user to specify characteristics (e.g., refractive index or n, k values) of the material(s) from which the measured sample feature is formed.

At operation 1704, a scatterometry user defines a nominal model of the expected sample structure by selecting one or more of the material files to assemble a stack of materials corresponding to those present in the periodic grating features to be measured. Such a user-defined model may be further parameterized through definition of nominal values of model parameters, such as thicknesses, critical dimension (CD), sidewall angle (SWA), height (HT), edge roughness, corner rounding radius, etc. which characterize the shape of the feature being measured. Depending on whether a two-dimensional model (i.e., a profile) or three-dimensional model is defined, it is not uncommon to have 30-50, or more, such model parameters.

From a parameterized model, simulated spectra for a given set of grating parameter values may be computed using rigorous diffraction modeling algorithms, such as Rigorous Coupled Wave Analysis (RCWA). Regression analysis is then performed at operation 1706 until the parameterized model converges on a set of parameter values characterizing a final profile model (for two-dimensional) that corresponds to a simulated spectrum which matches the measured diffraction spectra to a predefined matching criterion. The final profile model associated with the matching simulated diffraction signal is presumed to represent the actual profile of the structure from which the model was generated.

The matching simulated spectra and/or associated optimized profile model can then be utilized at operation 1708 to build a library of simulated diffraction spectra by perturbing the values of the parameterized final profile model. The resulting library of simulated diffraction spectra may then be employed by a scatterometry measurement system operating in a production environment to determine whether subsequently measured grating structures have been fabricated according to specifications. Library generation 1708 may include a machine learning system, such as a neural network, generating simulated spectral information for each of a number of profiles, each profile including a set of one or more modeled profile parameters. In order to generate the library, the machine learning system itself may have to undergo some training based on a training data set of spectral information. Such training may be computationally intensive and/or may have to be repeated for different models and/or profile parameter domains. Considerable inefficiency in the computational load of generating a library may be introduced by a user's decisions regarding the size of a training data set. For example, selection of an overly large training data set may result in unnecessary computations for training while training with a training data set of insufficient size may necessitate a retraining to generate a library.

For some applications it may be unnecessary to build a library. After the parametric model of the structure has been created and optimized, a regression analysis similar to that described above may be used in real time to determine the best fitting parameter values for each target as the diffraction beam data are collected. If the structure is relatively simple (for example a 2D structure), or if only a small number of parameters need to be measured, regression may be fast enough even though it may be slower than using a library. In other cases, the extra flexibility of using regression may justify some increase in measurement time over using a library. For a more detailed description of methods and systems that are capable of real-time regression of OCD data for use with the present invention, see U.S. Pat. No. 7,031,848, entitled REAL TIME ANALYSIS OF PERIODIC STRUCTURES ON SEMICONDUCTORS, filed on Jul. 8, 2005, which is incorporated herein by reference in its entirety.

Figure 18:
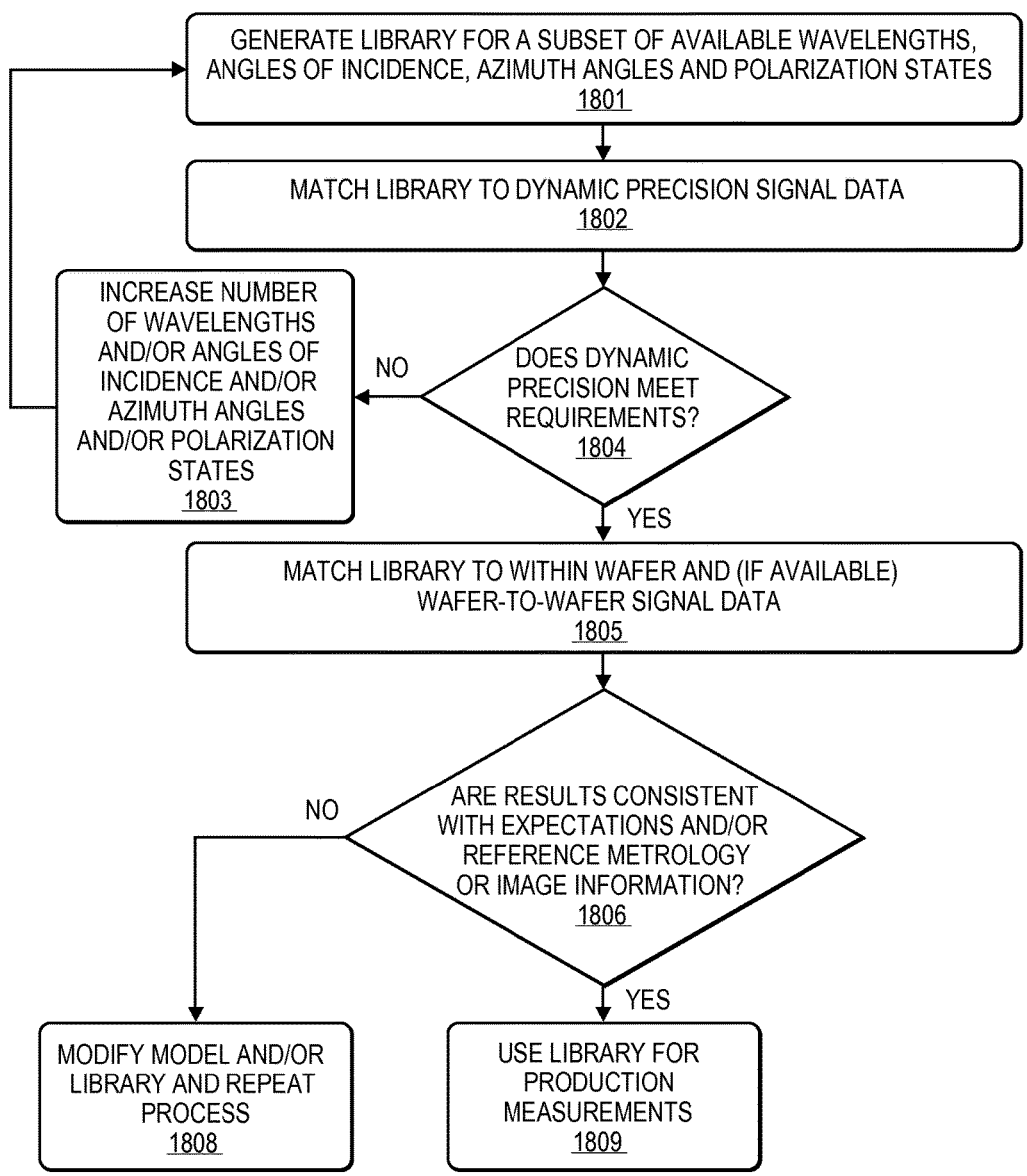
FIG. 18 is an illustrative flowchart representing operations in a method for building a library for making production measurements of a structure, in accordance with an embodiment of this invention.

FIG. 18 depicts a flowchart 1800 representing operations in a method of constructing and optimizing a library using an optical parametric model, in accordance with an embodiment of the present invention. Not every operation shown is always required. Some libraries may be optimized using a subset of the operations shown. It should be understood that some of these operations may be performed in a different sequence or that additional operations may be inserted into the sequence without departing from the scope of the present invention.

Referring to operation 1801, a library is created using a parametric model. That parametric model may have been created and optimized using a process such as one of the processes described in association with flowcharts 100, 200 or 300. The library is preferably created for a subset of the available wavelengths and angles in order to keep the library size small and to speed the library match or search. The library is then used to match dynamic precision signal data as shown at operation 1802 and hence determine the precision or repeatability of the measurement using that library. If the resulting precision does not meet requirements (operation 1804), then the number of wavelengths and/or angles and/or polarization states used needs to be increased as shown at operation 1803 and the process repeated. It is to be understood that if the dynamic precision is significantly better than required, it may be desirable to reduce the number of wavelengths and/or angles and/or polarization states in order to make a smaller, faster library. Embodiments of the present invention can be used to determine which additional wavelengths, angles or incidence, azimuth angles and/or polarizations states to include in the library.

When the library has been optimized for precision, any additional data that is available can be matched using that library as shown at operation 1805. The results from the larger set of data can be compared with reference data such as cross-section electron micrographs and also checked for consistency between wafers (for example, two wafers processed on the same equipment will usually show similar across-wafer variations) as shown at operation 1806. If the results meet expectations, then the library is ready for scatterometry measurements of production wafers (operation 1809). If the results do not meet expectations, then the library and/or parametric model need to be updated and the resulting new library retested (operation 1808). One or more embodiments of the present invention can used to determine what changes have to be made to the library or parametric model to improve the results.

Figure 19:
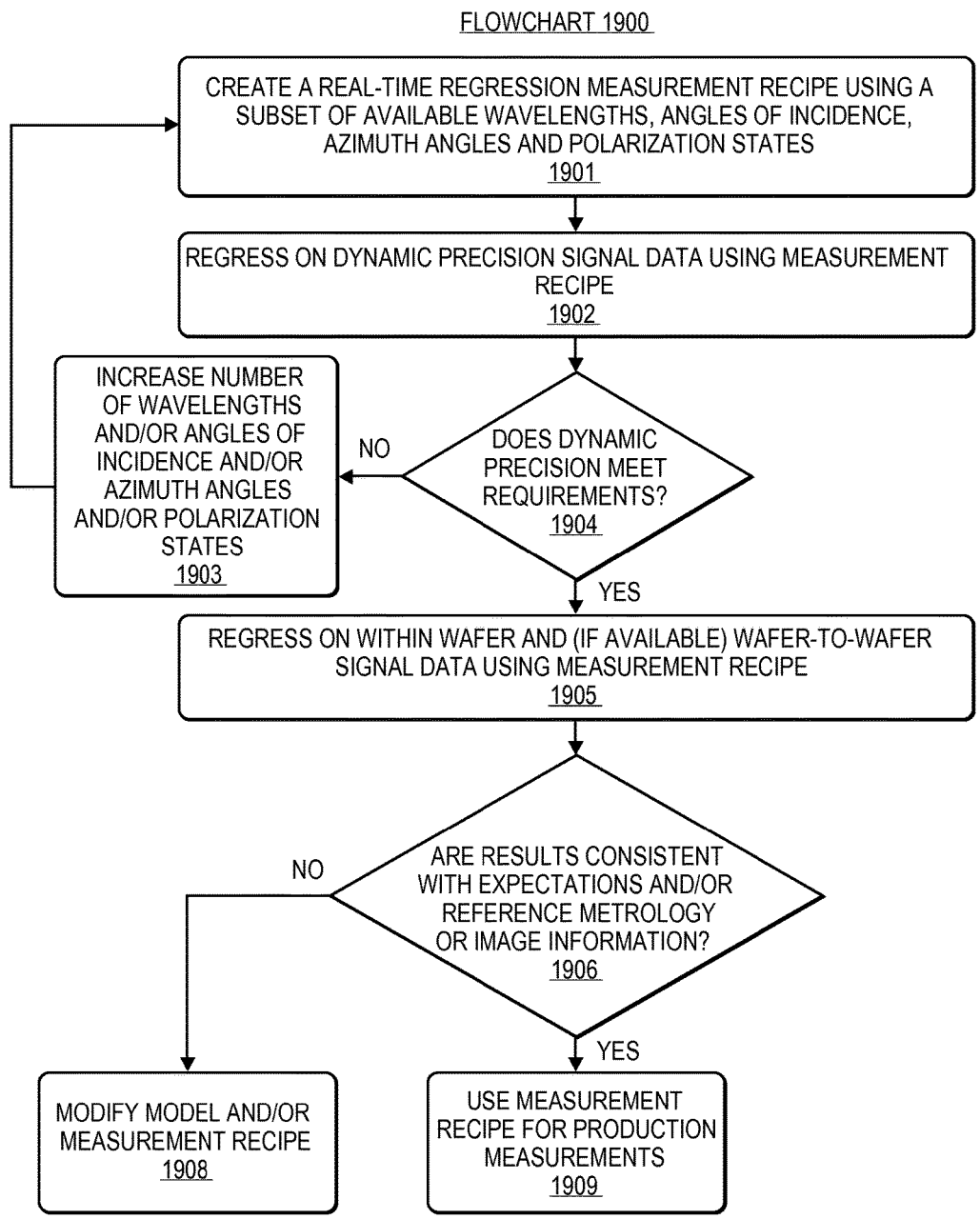
FIG. 19 is an illustrative flowchart representing operations in a method for building a real-time regression measurement recipe for making production measurements of a structure, in accordance with an embodiment of this invention.

FIG. 19 depicts a flowchart 1900 representing operations in a method of constructing and optimizing a real-time regression measurement recipe using an optical parametric model, in accordance with an embodiment of the present invention. Not every operation shown is always required. Some real-time regression measurement recipes may be optimized using a subset of the operations shown. It should be understood that some of these operations may be performed in a different sequence or that additional operations may be inserted into the sequence without departing from the scope of the present invention.

Referring to operation 1901, a real-time regression measurement recipe is created using a parametric model. That parametric model may have been created and optimized using a process such as the method described in association with one or more of flowcharts 100, 200 or 300. The recipe is preferably created for a subset of the available wavelengths and angles in order to keep the computation time as short as possible. The recipe is then used to regress on the dynamic precision signal data as shown at operation 1902 and hence determine the precision or repeatability of the measurement using that library. If the resulting precision does not meet requirements (operation 1904), then the number of wavelengths and/or angles and/or polarization states used needs to be increased as shown at operation 1903 and the process repeated. It is to be understood that if the dynamic precision is significantly better than required, it may be desirable to reduce the number of wavelengths and/or angles and/or polarization states in order to make a faster recipe. Embodiments of the present invention can be used to determine which additional wavelengths, angles or incidence, azimuth angles and/or polarizations states to include in the recipe.

When the recipe has been optimized for precision, any additional data that is available can be regressed using that recipe as shown at operation 1905. The results from the larger set of data can be compared with reference data such as cross-section electron micrographs and also checked for consistency between wafers (for example, two wafers processed on the same equipment will usually show similar across-wafer variations) as shown at operation 1906. If the results meet expectations, then the recipe is ready for scatterometry measurements of production wafers (operation 1909). If the results do not meet expectations, then the recipe and/or parametric model need to be updated and the resulting new recipe retested (operation 1908). One or more embodiments of the present invention can used to determine what changes have to be made to the recipe or parametric model to improve the results.

As illustrated in the above examples, the process of developing parametric models and libraries and real-time regression recipes that use those parametric models is often an iterative process. The present invention can significantly reduce the number of iterations required to arrive at parametric model and the libraries or real-time regression recipe using that model as compare with a trial-end-error approach. The present invention also significantly improves the measurement performance of the resulting parametric models, libraries and real-time regression recipes since the model parameters, wavelengths, angles of incidence, azimuthal angles and polarization states can all be chosen based on optimizing sensitivity and reducing correlations.

It is also to be understood that embodiments of the present invention also include the use of the techniques related to machine learning systems such as neural networks and support vector machines to generate simulated diffraction signals.

Thus, model optimization approaches based on spectral sensitivity have been disclosed. In accordance with an embodiment of the present invention, a method includes determining a first model of a structure. The first model is based on a first set of parameters. A set of spectral sensitivity variations data is determined for the structure. Spectral sensitivity is determined by derivatives of the spectra with respect to the first set of parameters. The first model of the structure is modified to provide a second model of the structure based on the set of spectral sensitivity variations data. The second model of the structure is based on a second set of parameters different from the first set of parameters. A simulated spectrum derived from the second model of the structure is then provided. In one embodiment, the method further involves comparing the simulated spectrum to a sample spectrum derived from the structure.

What is claimed is:
1. A method of optimizing parametric models for structural analysis using metrology of a semiconductor structure comprising repeating structures on a semiconductor substrate or wafer, the method comprising:
  determining a first model of a structure on the semiconductor substrate or wafer of the semiconductor structure, the first model based on a first set of parameters;
  calculating spectra for the first model of the structure for multiple points in parameter space using multiple different rays;
  determining a set of combined spectral sensitivity variations data for the structure for variation of the spectra calculated with respect to the parameters of the first model, wherein combined spectral sensitivity for the structure is determined by calculation of derivatives of the spectra for the multiple points in parameter space with respect to the first set of parameters;
  performing a spectral sensitivity analysis based on the set of combined spectral sensitivity variations data for the structure;
  modifying, based on the set of combined spectral sensitivity variations data for the structure and the spectral sensitivity analysis, the first model of the structure to provide a second model of the structure, the second model of the structure based on a second set of parameters different from the first set of parameters;
  calculating and providing a simulated spectrum derived from the second model of the structure;
  comparing the simulated spectrum derived from the second model to a sample spectrum derived from the structure on the semiconductor substrate or wafer of the semiconductor structure;
  identifying the simulated spectrum that matches the sample spectrum to a predetermined matching criterion;
  receiving the semiconductor structure comprising the repeating structures on the semiconductor substrate or wafer, wherein the semiconductor structure is fabricated according to a specification; and
  employing the identified simulated spectrum in a production environment to determine whether the semiconductor structure in the production environment has been fabricated according to the specification.

2. The method of claim 1, wherein modifying the first model of the structure to provide the second model of the structure further comprises reducing the degrees of freedom (DoF) of the first set of parameters to provide the second set of parameters.

3. The method of claim 2, wherein reducing the DoF of the first set of parameters comprises:
  generating the combined spectral sensitivity data for the structure;
  selecting an appropriate parameterization; and
  fixing parameters having a smallest combined spectral sensitivity.

4. The method of claim 1, wherein modifying the first model of the structure to provide the second model of the structure comprises reparameterizing geometric parameters or material parameters, or both, to provide the second set of parameters.

5. The method of claim 1, wherein modifying the first model of the structure to provide the second model of the structure comprises reparameterizing non-geometric parameters to provide the second set of parameters, the non-geometric parameters selected from the group consisting of custom function parameters and principal component analysis (PCA) parameters.

6. The method of claim 5, wherein the reparameterizing comprises using custom function parameters in linear or non-linear parameter correlations.

7. The method of claim 5, wherein the reparameterizing comprises using custom functions having different numbers of parameters.

8. The method of claim 5, wherein the reparameterizing comprises reducing a library size of the second set of parameters relative to the first set of parameters.

9. The method of claim 5, wherein the reparameterizing comprises using a discretized model having a large number of parameters.

10. The method of claim 3, wherein the combined spectral sensitivity data for the structure using multiple different rays is calculated for one or more of multiple Angles of Incidence (AOI), Azimuth angles, or Polarization states.

11. The method of claim 1, wherein the repeating structures comprise planar film stack structures located in the wafer scribe line area or device area, and the metrology comprises a thickness measurement.

12. The method of claim 1, wherein the repeating structures comprise repeating structures for measurement of critical dimension (CD) in the wafer scribe line area or device area.

13. The method of claim 1, wherein the repeating structures comprise a combination of structures for separate measurement as multiple targets, and for modeling together.

14. The method of claim 1, wherein performing the spectral sensitivity analysis includes performance of principal component analysis (PCA).

15. A system comprising:
  a fabrication cluster configured to fabricate a semiconductor structure comprising repeating structures on a semiconductor substrate or wafer, according to a specification; and
  an optical metrology system comprising
    a non-transitory machine-accessible storage medium having instructions stored thereon which cause a data processing system to perform a method of optimizing parametric models for structural analysis using metrology of repeating structures on a semiconductor substrate or wafer, the method comprising:
      determining a first model of a structure on a semiconductor substrate or wafer, the first model based on a first set of parameters;
      calculating spectra for the first model of the structure for multiple points in parameter space using multiple different rays;
      determining a set of combined spectral sensitivity variations data for the structure for variation of the spectra calculated with respect to the parameters of the first model, wherein combined spectral sensitivity is determined by calculation of derivatives of the calculated spectra for the multiple points in parameter space with respect to the first set of parameters;
      performing a spectral sensitivity analysis based on the set of combined spectral variations data for the structure;
      modifying, based on the set of combined spectral sensitivity variations data for the structure and the spectral sensitivity analysis, the first model of the structure to provide a second model of the structure, the second model of the structure based on a second set of parameters different from the first set of parameters;
      calculating and providing a simulated spectrum derived from the second model of the structure;

comparing the simulated spectrum derived from the second model to a sample spectrum derived from the structure on the semiconductor substrate or wafer;

identifying the simulated spectrum that matches the sample spectrum to a predetermined matching criteria; and employing the identified simulated spectrum in a production environment to determine whether the semiconductor structure has been fabricated according to the specification.

16. The system as in claim 15, wherein modifying the first model of the structure to provide the second model of the structure further comprises reducing the degrees of freedom (DoF) of the first set of parameters to provide the second set of parameters.

17. The system as in claim 16, wherein reducing the DoF of the first set of parameters comprises:

generating the combined spectral sensitivity data for the structure;

selecting an appropriate parameterization; and fixing parameters having a smallest combined spectral sensitivity.

18. The system as in claim 15, wherein modifying the first model of the structure to provide the second model of the structure comprises reparameterizing geometric parameters or material parameters, or both, to provide the second set of parameters.

19. The system as in claim 15, wherein modifying the first model of the structure to provide the second model of the structure comprises reparameterizing non-geometric parameters to provide the second set of parameters, the non-geometric parameters selected from the group consisting of custom function parameters and principal component analysis (PCA) parameters.

20. The system as in claim 19, wherein the reparameterizing comprises using custom function parameters in linear or non-linear parameter correlations.

21. The system as in claim 19, wherein the reparameterizing comprises using custom functions having different numbers of parameters.

22. The system as in claim 19, wherein the reparameterizing comprises reducing a library size of the second set of parameters relative to the first set of parameters.

23. The system as in claim 19, wherein the reparameterizing comprises using a discretized model having a large number of parameters.

24. The system as in claim 17, wherein the combined spectral sensitivity data for the structure using multiple different rays is calculated for one or more of multiple Angles of Incidence (AOI), Azimuth angles, or Polarization states.

25. The system as in claim 15, wherein the repeating structures comprise planar film stack structures located in the wafer scribe line area or device area, and the metrology comprises a thickness measurement.

26. The system as in claim 15, wherein the repeating structures comprise repeating structures for measurement of critical dimension (CD) in the wafer scribe line area or device area.

27. The system as in claim 15, wherein the repeating structures comprise a combination of structures for separate measurement as multiple targets, and for modeling together.

28. The system of claim 15, wherein performing the spectral sensitivity analysis includes performance of principal component analysis (PCA).

29. A system to generate a simulated diffraction signal to determine process parameters of a wafer application to fabricate a structure on a semiconductor substrate or wafer using optical metrology, the system comprising:

a fabrication cluster configured to perform a wafer application to fabricate a structure on a semiconductor substrate or wafer, wherein one or more process parameters characterize behavior of structure shape or layer thickness when the structure undergoes processing operations in the wafer application performed using the fabrication cluster; and an optical metrology system configured to determine the one or more process parameters of the wafer application, the optical metrology system comprising:

a beam source and detector configured to measure a diffraction signal of the structure; and a processor configured to determine a first model of a structure on a semiconductor substrate or wafer, the first model based on a first set of parameters, configured to calculate spectra for the first model of the structure for multiple points in parameter space using multiple different rays, configured to determine a set of combined spectral sensitivity variations data for the structure for variation of the spectra with respect to the parameters of the first model, wherein combined spectral sensitivity for the structure is determined by calculation of derivatives of the spectra for the multiple points in parameter space with respect to the first set of parameters, configured to perform a spectral sensitivity analysis of the set of combined spectral variations data for the structure, configured to modify the first model of the structure to provide a second model of the structure based on the set of combined spectral sensitivity variations data for the structure and the spectral sensitivity analysis, the second model of the structure based on a second set of parameters different from the first set of parameters, configured to calculate and provide a simulated spectrum derived from the second model of the structure, and configured to compare the simulated spectrum derived from the second model to a sample spectrum derived from the structure on the semiconductor substrate or wafer.

30. The system of claim 29, further comprising:

a library of simulated diffraction signals and values of one or more process parameters associated with the simulated diffraction signals, wherein the simulated diffraction signals were generated using values of one or more shape or film thickness parameters, and wherein the values of the one or more shape or film thickness parameters used to generate the simulated diffraction signals were derived from the values of the one or more process parameters associated with the simulated diffraction signals.

31. The system of claim 29, wherein performing the spectral sensitivity analysis includes performance of principal component analysis (PCA).

* * * * *